(12) United States Patent
Kim et al.

(10) Patent No.: US 7,479,254 B2
(45) Date of Patent: Jan. 20, 2009

(54) APPLICATION USING NON-COVALENT BOND BETWEEN A CUCURBITURIL DERIVATIVE AND A LIGAND

(75) Inventors: Kimoon Kim, Pohang (KR); Kangkyun Baek, Pohang (KR); Jeeyeon Kim, Pohang (KR); Iiha Hwang, Pohang (KR); Young Ho Ko, Pohang (KR); Narayanan Selvapalam, Pohang (KR); Erumaipatty R. Nagarajan, Pohang (KR); Kyeng Min Park, Pohang (KR)

(73) Assignees: Postech Foundation, Pohang (KR); Postech Academy-Industry Foundation, Pohang (KR)

( * ) Notice: Subject to any disclaimer, the term of this patent is extended or adjusted under 35 U.S.C. 154(b) by 370 days.

(21) Appl. No.: 11/407,143

(22) Filed: Apr. 20, 2006

(65) Prior Publication Data

US 2007/0092867 A1  Apr. 26, 2007

(30) Foreign Application Priority Data

| Oct. 20, 2005 | (KR) | ...................... 10-2005-0099379 |
| Nov. 12, 2005 | (KR) | ...................... 10-2005-0108312 |
| Jan. 4, 2006 | (KR) | ...................... 10-2006-0000891 |
| Feb. 24, 2006 | (KR) | ...................... 10-2006-0018434 |

(51) Int. Cl.
- *B01L 3/00* (2006.01)
- *A61K 9/36* (2006.01)
- *A61K 45/00* (2006.01)
- *C12Q 1/68* (2006.01)
- *G01N 15/06* (2006.01)
- *G01N 33/53* (2006.01)

(52) U.S. Cl. .................. 422/61; 422/68.1; 424/486; 424/489; 424/278.1; 424/280; 435/6; 435/7.1; 435/7.2

(58) Field of Classification Search .................. 422/61, 422/68.1; 424/486, 489, 278.1, 280; 435/6, 435/7.1, 7.2
See application file for complete search history.

(56) References Cited

U.S. PATENT DOCUMENTS 4,539,399 A  9/1985 Armstrong

FOREIGN PATENT DOCUMENTS

DE  19603377 A1  8/1997

(Continued)

OTHER PUBLICATIONS

Sasmal et al. "Facile Purification of Rare Cucurbiturils by Affinity Chromatography," Organic Letters, vol. 6, No. 8, pp. 1225-1228 (2004).

(Continued)

*Primary Examiner*—Jezia Riley
(74) *Attorney, Agent, or Firm*—Rothwell, Figg, Ernst & Manbeck

(57) ABSTRACT

Provided are a kit including a first component that is a compound of formula (1) below bound to a first material and a second component that is a ligand bound to a second material, wherein each of the first and second materials is independently selected from the group consisting of a solid phase, a biomolecule, an antioxidant, a chemical therapeutic agent, an anti-histaminic agent, a cucurbituril dendrimer, a cyclodextrin derivative, a crown ether derivative, a calixarene derivative, a cyclophane derivative, a cyclic peptide derivative, a metallic ion, a chromophore, a fluorescent material, a phosphor, a radioactive material, and a catalyst; and the ligand can non-covalently bind to the compound of formula (1); a method of separating and purifying a material bound to a ligand using the compound of formula (1) bound to a solid phase; a method of separating and purifying the compound of formula (1) or a material bound to the compound using a ligand bound to a solid phase; a sensor chip including a compound of formula (1) bound to a first material and a ligand bound to a second material; and a solid-catalyst complex including the compound of formula (1) bound to a first material and a ligand bound to a second material.

12 Claims, 17 Drawing Sheets

FOREIGN PATENT DOCUMENTS

| | | |
|---|---|---|
| EP | 1094065 A2 | 4/2001 |
| KR | 100263872 B1 | 5/2000 |

OTHER PUBLICATIONS

Freeman et al., "Cucurbituril," *J. Am. Chem Soc.*, vol. 103, pp. 7367-7368, 1981.

Clennan et al., "Additions of Singlet Oxygen to Alkoxy-Substituted butadienes. An Unexpectedly Large s-Cis/s-Trans Ratio in an (E,Z)-Diene or a Kinetic Anomeric Effect?," *J. Org. Chem.*, vol. 51, pp. 1440-1446, 1986.

Kellersberger et al., "Encapsulation of $N_2$, $O_2$, Methanol, or Acetonitrile by Decamethylcucurbit[5]uril($NH_4^+$)$_2$ Complexes in the Gas Phase: Influence of the Guest on 'Lid' Tightness," *J. Am. Chem. Soc.*, vol. 123, pp. 11316-11317, 2001.

Leibig, "Notification from the organic chemistry laboratory of The Technical Institute of Hanover" *Ann. Chem.*, 1905, vol. 339, pp. 1-37.

A.

B.

1    2    3

Myosin (200 K)

Phosphorylase B (97 K)

BSA (66 K)

Protein A (42 K)

Protein L (36 K)

Peanut Agglutinin (28 K)

Trypsin Inhibitor (20 K)

Lysozyme (14 K)
Aprotinin (6 K)

us 7,479,254 B2

APPLICATION USING NON-COVALENT BOND BETWEEN A CUCURBITURIL DERIVATIVE AND A LIGAND

CROSS-REFERENCE TO RELATED PATENT APPLICATIONS

This application claims the benefit of Korean Patent Application No. 10-2005-0099379, filed on Oct. 20, 2005, Korean Patent Application No. 10-2005-0108312, filed on Nov. 12, 2005, Korean Patent Application No. 10-2006-0000891, filed on Jan. 4, 2006, and Korean Patent Application No. 10-2006-0018434, filed on Feb. 24, 2006, in the Korean Intellectual Property Office, the disclosure of which is incorporated herein in its entirety by reference.

BACKGROUND OF THE INVENTION

1. Field of the Invention

The present invention relates to a kit comprising a first component that is a compound of formula (1) bound to a first material and a second component that is a ligand bound to a second material and capable of non-covalently binding to a cucurbituril derivative; a method of separating and purifying a material bound to a ligand using a compound of formula (1) bound to a solid phase; a method of separating and purifying a compound of formula (1) or a material bound to the compound of formula (1) using a ligand bound to a solid phase; a sensor chip comprising a complex of a compound of formula (1) bound to a first material and a ligand bound to a second material; and a solid-catalyst complex comprising a compound of formula (1) bound to a first material and a ligand bound to a second material.

2. Description of the Related Art

Host molecules, such as cyclodextrin (U.S. Pat. No. 4,539, 399), and crown ether (Korean Patent No. 026382), have the ability to retain guest molecules in their structure and thus research has been conducted into their application in separating and removing materials. To use such a host molecule as a column packing material, the host molecule has to be covalently bound to a solid substrate selected from among polymers, such as silica gel, zeolite, titanium oxide, cellulose, etc. Such host molecules covalently bound to solid substrates are used as stationary phases of various column packing materials for column chromatography and used to separate various samples.

Cucurbituril was first reported by R. Behrend, E. Meyer, F. Rusche in 1905 (*Liebigs Ann. Chem.* 1905, 339, 1). W. Mock et al. characterized cucurbituril as a hexameric macrocyclic compound having the chemical formula of $C_{36}H_{36}N_{24}O_{12}$ and confirmed the chemical structure by X-ray diffraction (*J. Am. Chem. Soc.* 1981, 103, 7367). They named this compound cucurbit[6]uril. Since then, improved synthetic methods of cucurbit[6]uril have been disclosed (refer to DE 196 03 377 A1).

Cucurbituril is a macrocyclic compound having a lipophilic cavity and two hydrophilic entrances at upper and lower portions. Accordingly, lipophilic interactions occur in the cavity of cucurbituril, and hydrogen bonds, polar-polar interactions, positive charge-polar interactions, etc. occur in the two entrances having n carbonyl groups. Therefore, cucurbituril has the ability to retain various compounds through more stable non-covalent bonding bond than commonly used cyclodextrin. In addition, cucurbituril has the ability to retain ionic materials and large-polarity materials, for examples, various organic materials, such as gaseous compounds, aliphatic compounds, aromatic compounds, etc., and various compounds, such as insecticides, herbicides, amino acids, nucleic acids, ionic compounds, metallic ions, organic metallic ions, etc. (J. Am. Chem. Soc. 2001, 123, 11316: European Patent No. 1094065; and J. Org. Chem. 1986, 51, and 1440).

SUMMARY OF THE INVENTION

The present invention provides a kit comprising a cucurbituril derivative bound to a particular material and a ligand bound to a particular material and capable of non-covalently binding to the cucurbituril derivative.

The present invention provides a method of separating and purifying a material bound to a ligand capable of non-covalently binding to a cucurbituril derivative using the cucurbituril derivative bound to a solid phase.

The present invention provides a method of separating and purifying a cucurbituril derivative capable of non-covalently binding to a ligand using the ligand bound to a solid phase, or a material bound to the cucurbituril derivative.

The present invention provides a sensor chip comprising a complex of a cucurbituril derivative bound to a particular material and a ligand bound to a particular material.

The present invention provides a solid-catalyst complex comprising a cucurbituril derivative bound to a particular material and a ligand bound to a particular material.

According to an aspect of the present invention, there is provided a kit comprising: a first component that is a compound of formula (1) bound to a first material; and a second component that is a ligand bound to a second material, wherein each of the first and second materials is independently selected from the group consisting of a solid phase, a biomolecule, an antioxidant, a chemical therapeutic agent, an anti-histaminic agent, a cucurbituril dendrimer, a cyclodextrin derivative, a crown ether derivative, a calixarene derivative, a cyclophane derivative, a cyclic peptide derivative, a metallic ion, a chromophore, a fluorescent material, a phosphor, a radioactive material, and a catalyst; and the ligand can non-covalently bind to a compound of formula (1) below, has at least one amine group, and is selected from the group consisting of a $C_1$-$C_{20}$ alkyl group; a $C_2$-$C_{20}$ alkenyl group; a $C_2$-$C_{20}$ alkynyl group; a $C_1$-$C_{20}$ alkoxy group; a $C_1$-$C_{20}$ aminoalkyl group; a $C_4$-$C_{20}$ cycloalkyl group; a $C_4$-$C_7$ heteroarylcyclo group; a $C_6$-$C_{20}$ aryl group; a $C_5$-$C_{20}$ heteroaryl group; a $C_1$-$C_{20}$ alkylsilyl group; a $C_6$-$C_{20}$ aryl group; a $C_5$-$C_{20}$ heteroaryl group; adamantane having a substituted or non-substituted $C_1$-$C_{20}$ alkyl group, $C_6$-$C_{20}$ aryl group or $C_5$-$C_{20}$ heteroaryl group; ferrocene or metallocene having a substituted or non-substituted $C_1$-$C_{20}$ alkyl group, $C_6$-$C_{20}$ aryl group or $C_5$-$C_{20}$ heteroaryl group; carborane having a substituted or non-substituted $C_1$-$C_{20}$ alkyl group, $C_6$-$C_{20}$ aryl group or $C_5$-$C_{20}$ heteroaryl group; fullerene having a substituted or non-substituted $C_1$-$C_{20}$ alkyl group, $C_6$-$C_{20}$ aryl group or $C_5$-$C_{20}$ heteroaryl group; cyclam or crown ether having a substituted or non-substituted $C_1$-$C_{20}$ alkyl group, $C_6$-$C_{20}$ aryl group or $C_5$-$C_{20}$ heteroaryl group; an oxygen-protected amino acid having a substituted or non-substituted $C_1$-$C_{20}$ alkyl group, $C_6$-$C_{20}$ aryl group or $C_5$-$C_{20}$ heteroaryl group; peptide having a substituted or non-substituted $C_1$-$C_{20}$ alkyl group, $C_6$-$C_{20}$ aryl group or $C_5$-$C_{20}$ heteroaryl group; alkaloid having a substituted or non-substituted $C_1$-$C_{20}$ alkyl group, $C_6$-$C_{20}$ aryl group or $C_5$-$C_{20}$ heteroaryl group; cisplatin having a substituted or non-substituted $C_1$-$C_{20}$ alkyl group, $C_6$-$C_{20}$ aryl group or $C_5$-$C_{20}$ heteroaryl group; oligonucleotide having a substituted or non-substituted $C_1$-$C_{20}$ alkyl group, $C_6$-$C_{20}$ aryl group or $C_5$-$C_{20}$ heteroaryl group; rhodamine having a substituted or non-substituted $C_1$-$C_{20}$ alkyl group, $C_6$-$C_{20}$ aryl group or $C_5$-$C_{20}$ heteroaryl group; and a nanoparticle having a substituted or non-substituted $C_1$-$C_{20}$ alkyl group, $C_6$-$C_{20}$ aryl group or $C_5$-$C_{20}$ heteroaryl group,

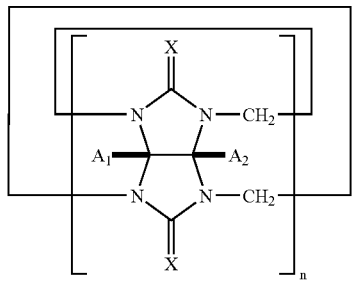

(1)

where n is an integer from 6 to 10;

X is O, S or NH;

each of $A_1$ and $A_2$ is independently H, OR, SR, or NHR, and $A_1$ and $A_2$ are not simultaneously H, where R is selected from the group consisting of H; a substituted or non-substituted $C_1$-$C_{30}$ alkyl group; a substituted or non-substituted $C_2$-$C_{30}$ alkenyl group; a substituted or non-substituted $C_2$-$C_{30}$ alkynyl group; a substituted or non-substituted $C_2$-$C_{30}$ carbonylalkyl group; a substituted or non-substituted $C_1$-$C_{30}$ thioalkyl group; a substituted or non-substituted $C_1$-$C_{30}$ alkylthiol group; a substituted or non-substituted $C_1$-$C_{30}$ hydroxyalkyl group; a substituted or non-substituted $C_1$-$C_{30}$ alkylsilyl group; a substituted or non-substituted $C_1$-$C_{30}$ aminoalkyl group; a substituted or non-substituted $C_1$-$C_{30}$ aminoalkylthioalkyl group; a substituted or non-substituted $C_5$-$C_{30}$ cycloalkyl group; a substituted or non-substituted $C_2$-$C_{30}$ heterocycloalkyl group; a substituted or non-substituted $C_6$-$C_{30}$ aryl group; a substituted or non-substituted $C_6$-$C_{30}$ arylalkyl group; a substituted or non-substituted $C_4$-$C_{30}$ heteroaryl group; and a substituted or non-substituted $C_4$-$C_{30}$ heteroarylalkyl group.

According to another aspect of the present invention, there is provided a method of separating and purifying a material bound to a ligand, the material being selected from the group consisting of a solid support or a biomolecule, an antioxidant, a chemical therapeutic agent, an anti-histaminic agent, a cucurbituril dendrimer, a cyclodextrin derivative, a crown ether derivative, a calixarene derivative, a cyclophane derivative, a cyclic peptide derivative, a metallic ion, a chromophore, a fluorescent material, a phosphorescent material, a radioactive material, and a catalyst, the method comprising: (a) preparing an affinity chromatography column filled with the compound of formula (1) above bound to a solid phase as a stationary phase; (b) supplying a mixture containing the material bound to a ligand into the affinity chromatography column; (c) washing the affinity chromatography column with a washing solution; and (d) loading a mobile phase solvent into the affinity chromatography column to separate and purify the material bound to the ligand.

According to another aspect of the present invention, there is provided a method of separating and purifying the compound of formula (1) above or a material bound to the compound, the material being selected from the group consisting of a solid support or a biomolecule, an antioxidant, a chemical therapeutic agent, an anti-histaminic agent, a cucurbituril dendrimer, a cyclodextrin derivative, a crown ether derivative, a calixarene derivative, a cyclophane derivative, a cyclic peptide derivative, a metallic ion, a chromophore, a fluorescent material, a phosphorescent material, a radioactive material, and a catalyst, the method comprising: (a) preparing an affinity chromatography column filled with a ligand bound to a solid phase as a stationary phase; (b) supplying a mixture containing the compound of formula (1) or the material bound to the compound into the affinity chromatography column; (c) washing the affinity chromatography column with a washing solution; and (d) loading a mobile phase solvent into the affinity chromatography column to separate and purify the compound of formula (1) or the material bound to the ligand.

According to another aspect of the present invention, there is provided a sensor chip comprising a compound of formula (1) above bound to a first material and a ligand bound to a second material, wherein one of the first and second materials is a solid phase, and the other is selected from the group consisting of an enzyme including histidine, cystein, or tryptophane, a substrate, a substrate analogue, a suppressor, a coenzyme, an antibody, an antigen, a virus, cell lectin, a polysaccharide, a glucoprotein, a cell surface receptor, a nucleic acid, a complementary base sequence, histone, a nucleic acid polymerase, a nucleic acid binding protein, ATP, ADP, a hormone, a vitamine, a receptor, a carrier protein, glutathione, a GST fusion protein, a metallic ion, a polyHIS fusion protein, a natural protein, and a combination thereof.

According to another aspect of the present invention, there is provided a solid-catalyst complex comprising the compound of formula (1) above bound to a first material and a ligand bound to a second material, wherein one of the first and second materials is a solid phase, and the other is a catalyst.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
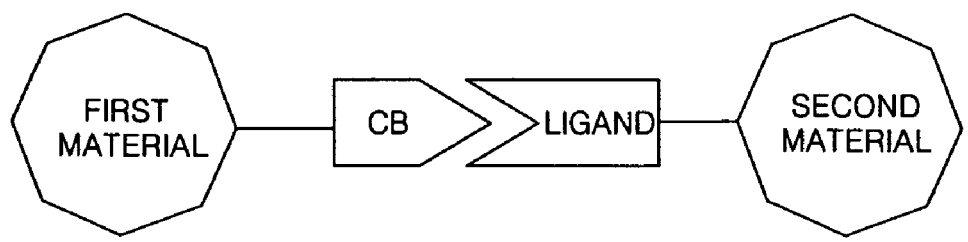
FIG. 1 schematically illustrates the non-covalently binding between cucurbit[7]uril bound to a solid phase and a ligand bound to a solid phase.

The inventors have found various applications of cucurbituril based on non-covalent bonding between the cucurbituril and a specific ligand and completed the invention.

Hereinafter, the present invention will be described in detail.

A kit according to the present invention includes: a first component that is a compound of formula (1) bound to a first material; and a second component that is a ligand bound to a second material.

The compound (cucurbituril derivative) of formula (1) of the first component and the ligand of the second component form a non-covalent bond as the ligand is inserted into a cavity of the cucurbituril derivative of formula (1).

Each of the first and second materials can be a solid phase as a solid support and a material having a particular function, such as a probe material, selected from the group consisting of a biomolecule, an antioxidant, a chemical therapeutic agent, an anti-histaminic agent, a cucurbituril dendrimer, a cyclodextrin derivative, a crown ether derivative, a calixarene derivative, a cyclophane derivative, a cyclic peptide derivative, a metallic ion, a chromophore, a fluorescent material, a phosphor, a radioactive material, and a catalyst.

In the kit according to the present invention, one of the first and second materials may be a biomolecule, and the other may be a chromophore, a fluorescent material, or a phosphor. This kit can be used to detect a particular material that can bind to or react with the biomolecule and further to detect the presence, position, or amount of the particular material, etc. For example, such a kit can be used in various analysis methods, for example, immunochemical staining, flow cytometry, in-situ hybridization, etc., based on the binding force between the compound of formula (1) of the first component and the ligand of the second component.

The solid phase that can be used as the first or second material in the kit according to the present invention may be a solid support selected from the group consisting of a polymer, a resin, a magnetic material, a silicagel, a polymer- or gold-coated silicagel, a zirconium oxide, a monolithic polymer, a polymer-coated magnetic particle, a gold thin film, a silver thin film, glass, an ITO-coated glass, silicon, a metal electrode, a nanorod, a nanotube, a nanowire, curdlan gum, cellulose, a nylon film, sepharose, and sephadex. For example, polystyrene resin or polymer-coated silicagel can be used as the solid phase.

When a halogen functional group (preferably, chloro group) exist on the surface of the solid phase, the halogen function group forms a covalent bond by the reaction with a functional group (for example, amine group) in the cucurbituril derivative or the ligand. As a result, the solid phase and the cucurbituril derivative or the ligand can be bound together.

Examples of the biomolecule that can be used as the first or second material in the kit according to the present invention include an enzyme, a nucleic acid, a protein, an amino acid, an antibody, an antigen, an inhibitor, a vitamin, a cofactor, a fatty acid, a cell, a cell membrane, a substrate, a substrate analogue, a suppressor, a coenzyme, a virus, lectin, a polysaccharide, a glucoprotein, a receptor, histone, ATP, ADP, a hormone, a receptor, glutathione, etc.

Examples of the enzyme, but are not limited to, include cellulase, hemicellulase, peroxidase, protease, amylase, xylanase, lipase, esterase, cutinase, pectinase, keratinase, reductase, oxidase, phenoloxidase, lipoxigenase, ligninase, pullulanase, arabinosidase, hyaluronidase, a combination thereof, etc.

Examples of the catalyst include, but are not limited to, a Grubbs catalyst, a radical initiator, a combination thereof, etc.

In an embodiment of the present invention, the compound of formula (1) may have an additional functional group. The functional group can be, for example, an amine group, a carboxyl group, etc., such as (aminoethylsulfanyl)propyl, (carboxyethylsulfanyl)propyl, etc.

In formula (1) above of the compound, which is a cucurbituril derivative, each of $A_1$ and $A_2$ can be independently H, OR, SR, or NHR where R is a substituted or non-substituted $C_2$-$C_{30}$ alkenyl group.

In formula (1) above, n may be 7, and X may be O.

The cucurbituril derivative, which is the compound of formula (1) of the first component and a particular ligand of the second component, which are included in the kit according to the present invention, bind together depending on pH. In particular, the cucurbituril derivative and the ligand form a complex in an acidic condition, whereas the complex dissociates in a basic condition. The cucurbituril derivative and the ligand non-covalently bind together in an acid solution of pH 8 or less with a binding constant of about $10^{10}$-$10^{15}$ $M^{-1}$, and maintain a dissociated state in an alkali solution of pH 8 or greater with a binding constant of about $10^0$-$10^4$ $M^{-1}$. The binding constant between the cucurbituril derivative and the ligand increases as the pH decreases, whereas the binding constant decreases as the pH increases and the solution changes to alkali A cucurbituril derivative that is the compound of formula (1) of the first component and a particular ligand of the second component can non-covalently bind together with a binding constant of about $10^0$-$10^{15}$ $M^{-1}$ according to the pH of a reaction solution. For example, a cucurbituril derivative with n=7 and an adamantane amine or ferrocene methylamine ligand can non-covalently bind together with a binding constant of about $10^{12}$ $M^{-1}$ or greater at pH 8 or less, and remain in a dissociated state with a binding constant of about $10^4$ $M^{-1}$ or less at pH 8 or greater.

When the binding constant between the cucurbituril derivative that is the compound of formula (1) of the first component and the particular ligand of the second component is $10^4$ $M^{-1}$ or less, their bond is weak and dissociates when a mobile solvent is flowed. When the binding constant is greater than $10^{10}$ $M^{-1}$, their bond is strong and unlikely dissociates.

In the kit according to the present invention, the ligand of the second component, which can non-covalently bind to the cucurbituril derivative, i.e., the compound of formula (1) of the first component may have at least one amine group and be selected from the group consisting of a $C_1$-$C_{20}$ alkyl group; a $C_2$-$C_{20}$ alkenyl group; a $C_2$-$C_{20}$ alkynyl group; a $C_1$-$C_{20}$ alkoxy group; a $C_1$-$C_{20}$ aminoalkyl group; a $C_4$-$C_{20}$ cycloalkyl group; a $C_4$-$C_7$ heteroarylcyclo group; a $C_6$-$C_{20}$ aryl group; a $C_5$-$C_{20}$ heteroaryl group; a $C_1$-$C_{20}$ alkylsilyl group; a $C_6$-$C_{20}$ aryl group; a $C_5$-$C_{20}$ heteroaryl group; adamantane having a substituted or non-substituted $C_1$-$C_{20}$ alkyl group, $C_6$-$C_{20}$ aryl group or $C_5$-$C_{20}$ heteroaryl group; ferrocene or metallocene having a substituted or non-substituted $C_1$-$C_{20}$ alkyl group, $C_6$-$C_{20}$ aryl group or $C_5$-$C_{20}$ heteroaryl group; carborane having a substituted or non-substituted $C_1$-$C_{20}$ alkyl group, $C_6$-$C_{20}$ aryl group or $C_5$-$C_{20}$ heteroaryl group; fullerene having a substituted or non-substituted $C_1$-$C_{20}$ alkyl group, $C_6$-$C_{20}$ aryl group or $C_5$-$C_{20}$ heteroaryl group; cyclam or crown ether having a substituted or non-substituted $C_1$-$C_{20}$ alkyl group, $C_6$-$C_{20}$ aryl group or $C_5$-$C_{20}$ heteroaryl group; an oxygen-protected amino acid having a substituted or non-substituted $C_1$-$C_{20}$ alkyl group, $C_6$-$C_{20}$ aryl group or $C_5$-$C_{20}$ heteroaryl group; peptide having a substituted or non-substituted $C_1$-$C_{20}$ alkyl group, $C_6$-$C_{20}$ aryl group or $C_5$-$C_{20}$ heteroaryl group; alkaloid having a substituted or non-substituted $C_1$-$C_{20}$ alkyl group, $C_6$-$C_{20}$ aryl group or $C_5$-$C_{20}$ heteroaryl group; cisplatin having a substituted or non-substituted $C_1$-$C_{20}$ alkyl group, $C_6$-$C_{20}$ aryl group or $C_5$-$C_{20}$ heteroaryl group; oligonucleotide having a substituted or non-substituted $C_1$-$C_{20}$ alkyl group, $C_6$-$C_{20}$ aryl group or $C_5$-$C_{20}$ heteroaryl group; rhodamine having a substituted or non-substituted $C_1$-$C_{20}$ alkyl group, $C_6$-$C_{20}$ aryl group or $C_5$-$C_{20}$ heteroaryl group; and a nanoparticle having a substituted or non-substituted $C_1$-$C_{20}$ alkyl group, $C_6$-$C_{20}$ aryl group or $C_5$-$C_{20}$ heteroaryl group, For example, the ligand can be adamantane, ferrocene, or metallocene that have at least one amine group and a substituted or non-substituted $C_1$-$C_{20}$ alkyl group, $C_6$-$C_{20}$ aryl group or $C_5$-$C_{20}$ heteroaryl group. The amine group may be a primary amine, a secondary amine, or a hydrogenated amine. For example, the ligand can be adamantanamine or ferrocene methylamine.

According to the present invention, a material bound to a ligand can be separated or purified using the non-covalent binding between a cucurbituril derivative and the ligand.

According to another aspect of the present invention, there is provided a method of separating and purifying a material bound to a ligand, the material being selected from the group consisting of a biomolecule, an antioxidant, a chemical therapeutic agent, an anti-histaminic agent, a cucurbituril dendrimer, a cyclodextrin derivative, a crown ether derivative, a calixarene derivative, a cyclophane derivative, a cyclic peptide derivative, a metallic ion, a chromophore, a fluorescent material, a phosphor, a radioactive material, and a catalyst, the method comprising: (a) preparing an affinity chromatography column filled with a compound of formula (1) bound to a solid phase as a stationary phase; (b) supplying a mixture containing the material bound to a ligand into the affinity chromatography column; (c) washing the affinity chromatography column with a washing solution; and (d) loading a mobile phase solvent into the affinity chromatography column to separate and purify the material bound to the ligand.

The affinity chromatography column used in the method can be any column commonly used in the field.

Examples of the biomolecule that can be used in the method according to the present invention include an enzyme, a nucleic acid, a protein, an amino acid, an antibody, an antigen, an inhibitor, a vitamin, a cofactor, a fatty acid, a cell, a cell membrane, a substrate, a substrate analogue, a suppressor, a coenzyme, a virus, lectin, a polysaccharide, a glucoprotein, a receptor, histone, ATP, ADP, a hormone, a receptor, glutathione, etc. Examples of the enzyme include cellulase, hemicellulase, peroxidase, protease, amylase, xylanase, lipase, esterase, cutinase, pectinase, keratinase, reductase, oxidase, phenoloxidase, lipoxigenase, ligninase, pullulanase, arabinosidase, hyaluronidase, a combination thereof, etc.

The ligand that can be used in the method of separating and purifying a material bound to the ligand can non-covalently bind to the compound of formula (1) and has at least one amine group. Such a ligand is selected from the group consisting of a C1-C20 alkyl group; a C2-C20 alkenyl group; a C2-C20 alkynyl group; a C1-C20 alkoxy group; a C1-C20 aminoalkyl group; a C4-C20 cycloalkyl group; a C4-C7 heteroarylcyclo group; a C6-C20 aryl group; a C5-C20 heteroaryl group; a C1-C20 alkylsilyl group; a C6-C20 aryl group; a C5-C20 heteroaryl group; adamantane having a substituted or non-substituted C1-C20 alkyl group, C6-C20 aryl group or C5-C20 heteroaryl group; ferrocene or metallocene having a substituted or non-substituted C1-C20 alkyl group, C6-C20 aryl group or C5-C20 heteroaryl group; carborane having a substituted or non-substituted C1-C20 alkyl group, C6-C20 aryl group or C5-C20 heteroaryl group; fullerene having a substituted or non-substituted C1-C20 alkyl group, C6-C20 aryl group or C5-C20 heteroaryl group; cyclam or crown ether having a substituted or non-substituted C1-C20 alkyl group, C6-C20 aryl group or C5-C20 heteroaryl group; an oxygen-protected amino acid having a substituted or non-substituted C1-C20 alkyl group, C6-C20 aryl group or C5-C20 heteroaryl group; peptide having a substituted or non-substituted C1-C20 alkyl group, C6-C20 aryl group or C5-C20 heteroaryl group; alkaloid having a substituted or non-substituted C1-C20 alkyl group, C6-C20 aryl group or C5-C20 heteroaryl group; cisplatin having a substituted or non-substituted C1-C20 alkyl group, C6-C20 aryl group or C5-C20 heteroaryl group; oligonucleotide having a substituted or non-substituted C1-C20 alkyl group, C6-C20 aryl group or C5-C20 heteroaryl group; rhodamine having a substituted or non-substituted C1-C20 alkyl group, C6-C20 aryl group or C5-C20 heteroaryl group; and a nanoparticle having a substituted or non-substituted C1-C20 alkyl group, C6-C20 aryl group or C5-C20 heteroaryl group.

The method of separating and purifying a material bound to a ligand according to the present invention may further include binding the compound of formula (1) to the solid phase before operation (a). To this end, the compound of formula (1) may have an additional functional group. The functional group can be, for example, an amine group, a carboxyl group, etc., such as (aminoethylsulfanyl)propyl, (carboxyethylsulfanyl)propyl, etc.

The method of separating and purifying a material bound to a ligand may further include binding the ligand and the material between operations (a) and (b).

The compound of formula (1) and the solid phase, or the ligand and the solid phase may be covalently bound together.

Examples of the mobile solvent that can be used in the method of separating and purifying a material bound to a ligand according to the present invention include methanol, trifluoracetic acid, triethylamine, methylene chloride, chloroform, dimethylformamide, dimethyl sulfoxide, toluene, acetonitrile, xylene, chlorobenzine, tetrahydrofurane, diethylether, ethanol, diglycol ether, silicon, supercritical carbon dioxide, ionic liquids, N-methylpyrrolidine, pyridine, water, ammonium hydroxide, dioxane, etc.

Examples of the washing solution that can be used in the method of separating and purifying a material bound to a ligand according to the present invention include methanol, trifluoracetic acid, triethylamine, methylene chloride, chloroform, dimethylformamide, dimethyl sulfoxide, toluene, acetonitrile, xylene, chlorobenzine, tetrahydrofurane, diethylether, ethanol, diglycol ether, silicon, supercritical carbon dioxide, ionic liquids, N-methylpyrrolidine, pyridine, water, ammonium hydroxide, dioxane, etc.

The present invention also provides a method of separating and purifying a compound of formula (1) or a material bound to the compound, the material being selected from the group consisting of a biomolecule, an antioxidant, a chemical therapeutic agent, an anti-histaminic agent, a cucurbituril dendrimer, a cyclodextrin derivative, a crown ether derivative, a calixarene derivative, a cyclophane derivative, a cyclic peptide derivative, a metallic ion, a chromophore, a fluorescent material, a phosphor, a radioactive material, and a catalyst, the method comprising: (a) preparing an affinity chromatography column filled with a ligand bound to a solid phase as a stationary phase; (b) supplying a mixture containing the compound of formula (1) or the material bound to the compound into the affinity chromatography column; (c) washing the affinity chromatography column with a washing solution; and (d) loading a mobile phase solvent into the affinity chromatography column to separate and purify the compound of formula (1) or the material bound to the ligand, The method of separating and purifying the compound of formula (1) or a material bound to the compound may further include binding the ligand to the solid phase before operation (a).

When separating and purifying a material bound to the compound of formula (1), the method may further include binding the compound of formula (1) and the material between operations (a) and (b). To this end, the compound of formula (1) may have an additional functional group. The functional group can be, for example, an amine group, a carboxyl group, etc., such as (aminoethylsulfanyl)propy, (carboxyethylsulfanyl)propyl, etc.

The washing solution and the mobile phase solvent used in the method of separating and purifying the compound of formula (1) or a material bound to the compound according to the present invention may be the same as used in the method of separating and purifying a material bound to the ligand described above.

When an additional purification process, such as dialysis, etc., is performed on a solution recovered from the column in the above-described separating and purifying method, a higher purity material can be obtained.

The cucurbituril derivative of formula (1) bound to a solid phase or a particular material form a stable complex with a ligand bound to a solid phase or a particular material with a strong binding force that remains after the removal of a solvent. Whether the cucurbituril derivative of formula (1) and a ligand can bind together depends on the type of solvent, pH, polarity, temperature, and electrical change.

In order to induce the binding of the cucurbituril derivative of formula (1) and the ligand, a condition allowing the hydrogenation of the amine group of the ligand or an acidic condition is required. In order to dissociate the bind of the cucurbituril derivative and the ligand, a dehydrogenation condition or an alkali condition is required.

According to the present invention, a material can be separated or purified using the non-covalent bonding between the compound of formula (1) and a ligand. In particular, a particular component bound to a ligand in a mixture can be separated or purified using the compound of formula (1) bound to a solid phase. In addition, the compound of formula (1) in a mixture or a particular compound bound to the compound of formula (1) can be separated using a ligand bound to a solid phase.

In particular, a method of using a magnetic material (magnet) for the solid phase, a method of using a filter, etc., can be used to easily separate such a particular component as described above.

Further, when an additional dialysis process, etc., is performed after the method of using a magnet or filter, a higher purity material can be obtained.

In the method of using a magnet or filter, methanol, trifluoracetic acid, triethylamine, methylene chloride, chloroform, dimethylformamide, dimethyl sulfoxide, toluene, acetonitrile, xylene, chlorobenzine, tetrahydrofurane, diethylether, ethanol, diglycol ether, silicon, supercritical carbon dioxide, ionic liquids, N-methylpyrrolidine, pyridine, water, ammonium hydroxide, dioxane, etc., can be used as a solvent.

According to another aspect of the present invention, there is provided a sensor chip comprising a complex of the compound of formula (1) bound to a first material and a ligand bound to a second material.

Sensor chips are devices with a probe material (for example, biomolecule, etc.) on a solid substrate to detect a target material.

In the sensor chip according to the present invention, one of the first and second materials is a solid phase, and the other is a probe material.

In the sensor chip according to the present invention, the solid phase that can be used as the first or second material may be a solid support, such as a gold thin film, a silver thin film, or an ITO-coated glass.

Examples of the probe materials that can be used as the first or second material include, but are not limited to, an enzyme, such as histidine, cystein, or tryptophane, a substrate, a substrate analogue, a suppressor, a coenzyme, an antibody, an antigen, a virus, cell lectin, a polysaccharide, a glucoprotein, a cell surface receptor, a nucleic acid, a complementary base sequence, histone, a nucleic acid polymerase, a nucleic acid binding protein, ATP, ADP, a hormone, a vitamine, a receptor, a carrier protein, glutathione, a GST fusion protein, a metallic ion, a polyHIS fusion protein, a natural protein, a combination thereof, etc. Examples of the enzyme include cellulase, hemicellulase, peroxidase, protease, amylase, xylanase, lipase, esterase, cutinase, pectinase, keratinase, reductase, oxidase, phenoloxidase, lipoxigenase, ligninase, pullulanase, arabinosidase, hyaluronidase, a combination thereof, etc.

The sensor chip according to the present invention can confirm the detection of a target material through an electrochemical method, an optochemical method, a fluorescent method, a phosphorescent method, HPLC, gas chromatography, NMR, EPR, an isotropic method, etc.

The sensor chip according to the present invention can be used as a biosensor or bio-fuel cell electrode when the probe material is a biomolecule.

According to another aspect of the present invention, there is provided a solid-catalyst complex comprising a compound of formula (1) below bound to a first material and a ligand bound to a second material, wherein one of the first and second materials is a solid phase, and the other is a catalyst.

In the solid-catalyst complex according to the present invention, the catalyst may be a Grubbs catalyst, a radical initiator, or a combination thereof.

In the solid-catalyst complex according to the present invention, the catalyst may be selected from the group consisting of cellulase, hemicellulase, peroxidase, protease, amylase, xylanase, lipase, esterase, cutinase, pectinase, keratinase, reductase, oxidase, phenoloxidase, lipoxigenase, ligninase, pullulanase, arabinosidase, hyaluronidase, and a combination thereof.

Examples of the solid phase that can be used in the solid-catalyst complex according to the present invention include a polymer, a resin, a magnetic material, a silicagel, a polymer- or gold-coated silicagel, a zirconium oxide, a monolithic polymer, a polymer-coated magnetic particle, a gold thin film, a silver thin film, glass, an ITO-coated glass, silicon, a metal electrode, a nanorod, a nanotube, a nanowire, curdlan gum, cellulose, a nylon film, sepharose, sephadex, etc. In particular, the solid phase can be polystyrene resin or polymer-coated silicagel.

The solid-catalyst complex according to the present invention can be repeatedly used unlit the catalytic activity disappears and provides a catalytic function through an organic reaction at room temperature. For a catalytic function, various buffer solutions suitable for reactions can be used. Examples of buffer solutions that can be used include methanol, trifluoracetic acid, triethylamine, methylene chloride, chloroform, dimethylformamide, dimethyl sulfoxide, toluene, acetonitrile, xylene, chlorobenzine, tetrahydrofurane, diethylether, ethanol, diglycol ether, silicon, supercritical carbon dioxide, ionic liquids, N-methylpyrrolidine, pyridine, water, ammonium hydroxide, dioxane, etc.

Whether a cucurbituril derivative and a ligand respectively bound to particular materials have bound together can be conformed through Fourier Transform Infrared (FT-IR) absorption measurement.

Hereinafter, the present invention will be described in greater detail with reference to the following examples. The following examples are only for illustrative purposes and are not intended to limit the scope of the invention.

EXAMPLE 1

Synthesis of Cucurbit[7]uril

After melting glycouryl (5.7 g, 40 mmol) in 20 mL of sulfuric acid (9 M), an aqueous formaldehyde solution (7.0 mL, 91 mmol) was added. The resultant reaction mixture was stirred at 75 ☐ for 24 hours. The temperature was raised to 95-100☐, and the reaction was further performed. 200 mL of water was quickly poured into the reaction mixture, and 1 L of acetone was further added to obtain a precipitate. The precipitate was filtered under reduced pressure and washed with a 1:4 mixed solution of water and acetone. The solid filtrate was dissolved in 200 mL of a 1:1 mixed solution of water and acetone and filtered under reduced pressure to remove a precipitate (cucurbit[6]uril).

800 mL of acetone was added to the filtrate to precipitate a mixture of cucurbit[7]uril and cucurbit[5]uril. The precipitated mixture of cucurbit[7]uril and cucurbit[5]uril was dissolved in 40 mL of water, and 25 mL of methanol was added to precipitate only cucurbit[7]uril. The precipitated cucurbit[7]uril was filtered under reduced pressure and dried in a vacuum. The results of an analysis are as follows.

$^1$H NMR (500 MHz, $D_2O$): δ=5.56 (d, 14H), 5.35 (s, 14H), 4.11 (d, 14H).

EXAMPLE 2

Synthesis of Hydroxycucurbit[7]uril

Cucurbit[7]uril (10 g, 8.6 mmol) synthesized in Example 1 and $K_2S_2O_8$ (39 g, 145 mmol) were added to 450 mL of distilled water and subjected to ultrasonication for 10 minutes. Next, the temperature was raised to 85° C., and the reaction was performed for 12 hours. The reaction mixture was cooled to room temperature to obtain a white precipitate. The precipitate was removed through filtration under reduced pressure. A solvent in the filtrate was vaporized to obtain hydroxycucurbit[7]uril. The degree of substitution of hydroxycucurbit[7]uril was about 0.8. The degree of substitution of hydroxycucurbit[7]uril refers to the ratio of substitution of hydrogen ($A_1$ and $A_2$ in formula 1) in cucurbit[7]uril by hydroxyl groups.

$^1$H-NMR (500 MHz, DMSO-$d_6$): δ=7.83 (s, 11H), 5.68-5.12 (d, 17H), 4.42 (d, 14H);

$^{13}$C-NMR (125 MHz, DMSO-$d_6$): δ=152.7, 93.8, 40.2.

EXAMPLE 3

Synthesis of Allyloxycucurbit[7]uril

Hydroxycucurbit[7]uril (1.2 g, 0.92 mmol) synthesized in Example 2 was added into an anhydrous DMSO solution (150 mL) and dissolved. NaH (0.89 g, 22.4 mmol) was added into the solution. The reaction mixture was stirred in an argon atmosphere at room temperature for 1 hour, and aryl bromide (2.0 mL, 22.0 mmol) was slowly added into the reaction mixture at 0° C. while stirring. After the reaction mixture was further stirred at room temperature for 12 hours, an excess of water was added into the reaction mixture to precipitate allyloxycucurbit[7]uril. The degree of substitution of the obtained allyloxycucurbit[7]uril was about 0.7.

EXAMPLE 4

Synthesis of Solid-Phase
(Polystyrene-co-DVD-NCO)

Figure 2:
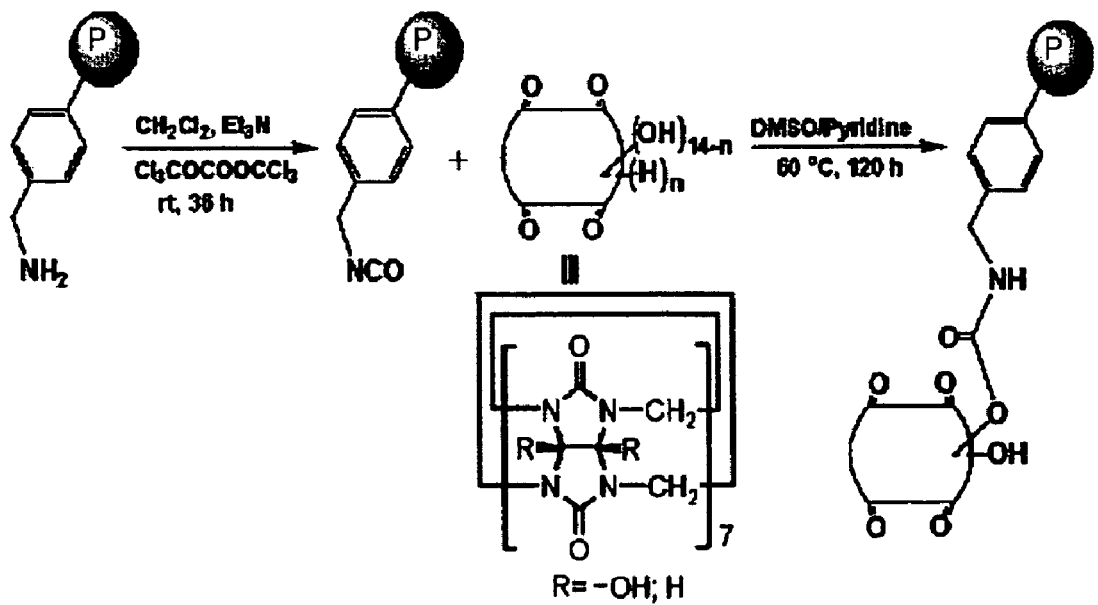
FIG. 2 illustrates the reaction of obtaining polystyrene-co-DVB-NCO from polystyrene-co-DVB-NH$_2$ and the reaction of immobilizing hydroxycucurbit[7]uril on polystyrene-co-DVB-NCO.

After amine-functionalized polystyrene-co-divinylbenzene (polystyrene-co-DVB-$NH_2$, Aldrich Corp., 30-60 mesh, 2.5 mmol N/g, 5.0 g, 12.5 mmol or 30) as a polymeric resin was added into 50 mL of dichloromethane, triethylamine (9.6 mL, 69 mmol) and triphosgen (2.7 g, 9.1 mmol) were added into the mixture and shaken at room temperature for 36 hours. After filtration under reduced pressure, the resulting filter cake was washed with dichloromethane, chloroform, ether, and then tetrahydrofurane and dried in a vacuum dried for 24 hours to obtain isocyanatemethyl polystyrene-co-divinylbenzene (polystyrene-co-DVB-NCO), polymeric resin with an isocyanate group substituted for the amine group (FIG. 2).

Figure 3:
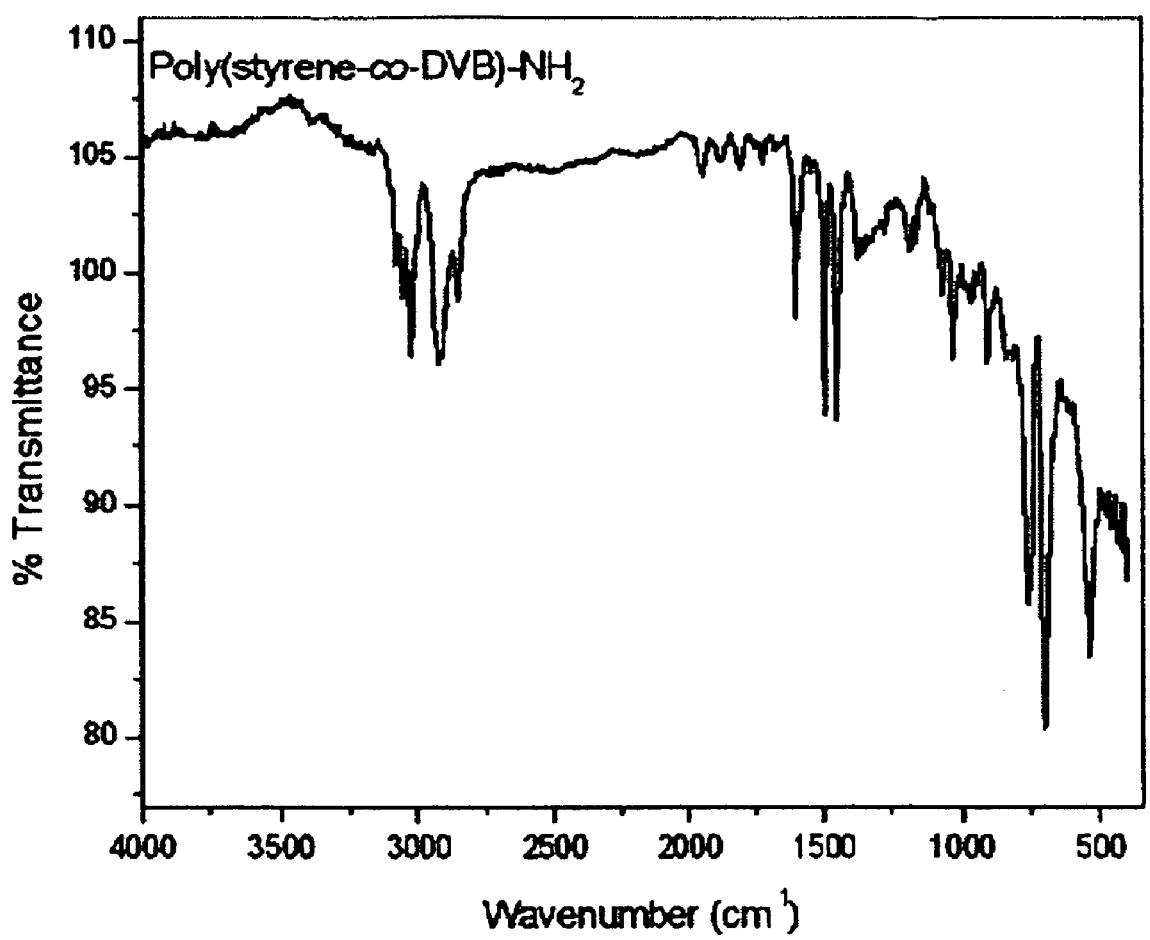
FIGS. 3 and 4 are the FT-IR spectra of polystyrene-co-DVB-NH$_2$ and polystyrene-co-DVB-NCO, respectively.
Figure 4:
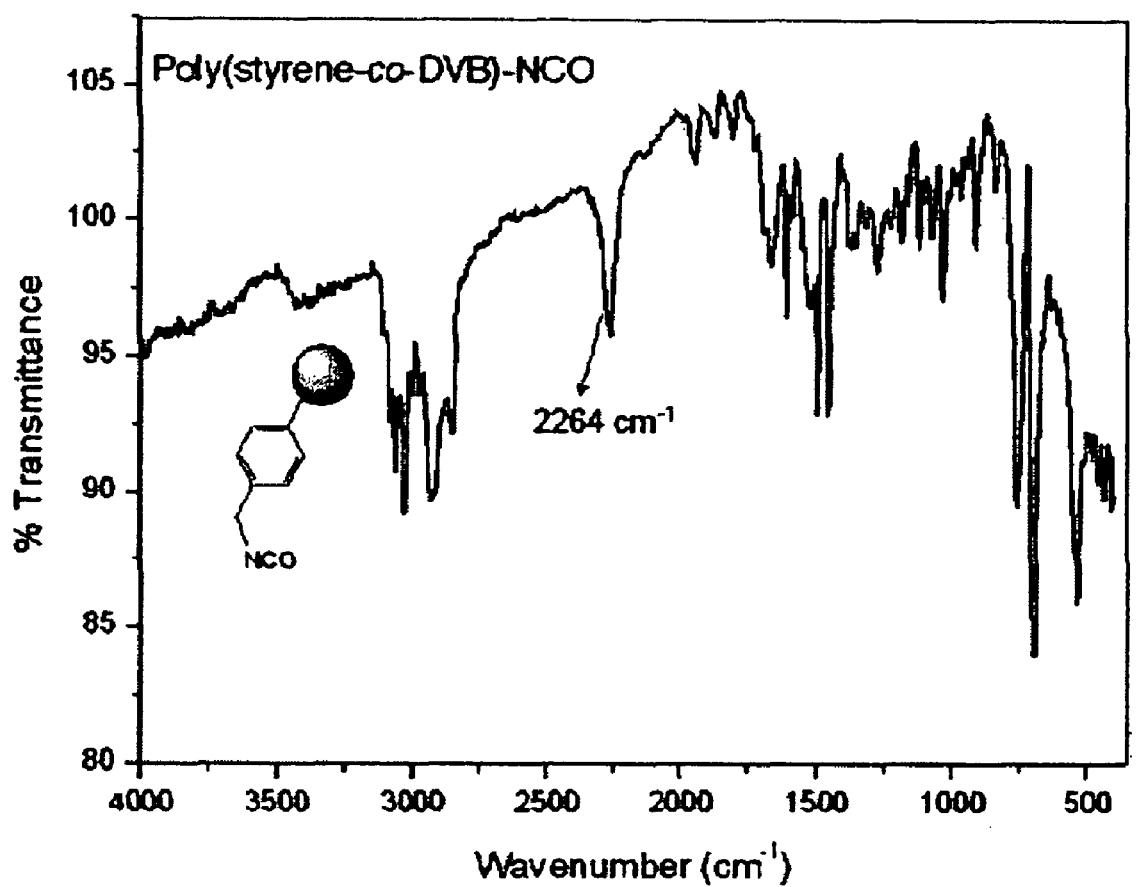

Comparing the IR spectrum of polystyrene-co-DVB-$NH_2$ of FIG. 3 and the IR spectrum of polystyrene-co-DVB-NCO of FIG. 4, a new peak of the isocyanate group (—NCO) appears near 2264 $cm^{-1}$ in the IR spectrum of FIG. 4.

The results of measuring the IR spectrum of polystyrene-co-DVB-NCO in FIG. 4 are as follows.

IR (KBr): 3027, 2929, 2264, 1659, 1602, 1494, 1452, 1269, 1116, 1029 cm$^{-1}$

EXAMPLE 5

Immobilization of Hydroxycucurbit[7]uril onto Solid-Phase

After the solid-phase polystyrene-co-DVB-NCO polymer resin (2.0 g, 2.5 mmol N/g) obtained in Example 4 was swelled with 8 mL of dimethyl sulfuroxide, a solution of the hydroxycucurbit[7]uril (1.44 g, 1.2 mmol) obtained in Example 2 in a mixture of dimethyl sulfuroxide/pyridine (37 mL/3 mL) was added and stirred at 60° C. in an argon environment for 120 hours to be uniformly mixed (FIG. 2). Next, the reaction mixture was filtered under reduced pressure, washed several times with dimethyl sulfoxide, methanol, water, and ether, and dried at 50° C. in a vacuum for 24 hours to immobilize hydroxycucurbit[7]uril onto the solid-phase. The results of measuring the IR spectrum of the immobilized hydroxycucurbit[7]uril are as follows (refer to FIG. 5)

IR (KBr): 3026, 2920, 1755, 1689, 1602, 1493, 1452, 1272, 1115, 1028 cm$^{-1}$.

Figure 5:
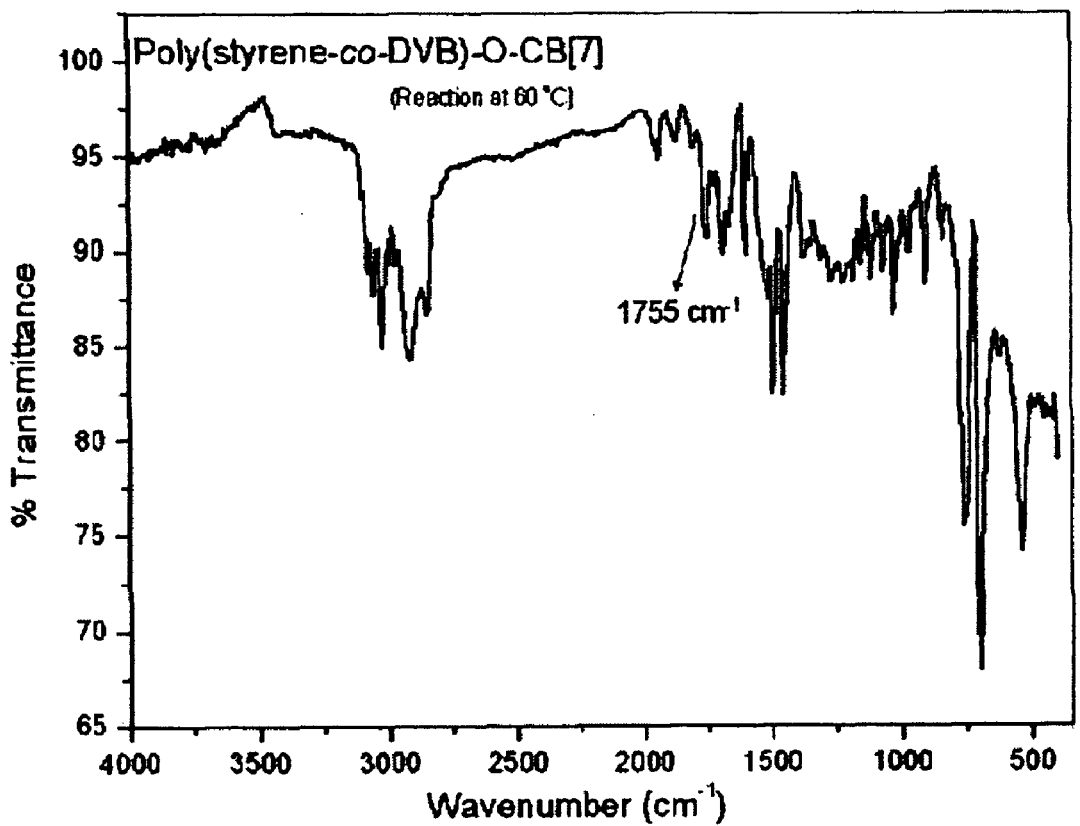
FIG. 5 is the FT-IR spectrum of polystyrene-co-DVB-CO-hydroxycucurbit[7]uril obtained by immobilizing hydroxycucurbit[7]uril on polystyrene-co-DVB-NCO.

Referring to FIG. 5, the peak of isocyanate group near 2264 cm$^{-1}$ in FIG. 4 disappears, and a new peak of carbonyl carbon in the hydroxycucurbit[7]uril appears at 1755 cm$^{-1}$. In addition, it was confirmed through an element analysis that 75-110 μmol of hydroxycucurbit[7]uril per 1 g of the solid phase had been immobilized.

EXAMPLE 6

Preparation of Solid-Phase (1) Chloromethylation of Porous Polystyrene (Cross-Linked with 1% Divinylbenzene)

After 3 g of porous polystyrene CombiGel XE-305 (Aldrich Corp.) (cross-linked with 1% divinylbenzene) was mixed with chloromethyl methylether (29.90 g, 0.38 mmol), SnCl$_4$ (0.90 mL) was dropwise added into the mixture at 0° C. The reaction mixture was refluxed at 59° C. for 4.5 hours. The colorless CombiGel XE-305 gradually changed red. A methanol solution was added to neutralize the reaction mixture until the red color disappeared. The polymeric resin was filtered through a glass filter with methanol, tetrahydrofurane (THF), and water to obtain chloromethylated polystyrene (cross-linked with 1% divinylbenzene) in white powder form. The results of an element analysis are as follows.

Element analysis: C, 68.68; H, 6.01; Cl, 18.35%

As is apparent from the results of the element analysis, 5.2 mmol of chlorine exists per 1 g of chloromethylated polystyrene (cross-linked with 1% divinylbenzene).

Figure 7:
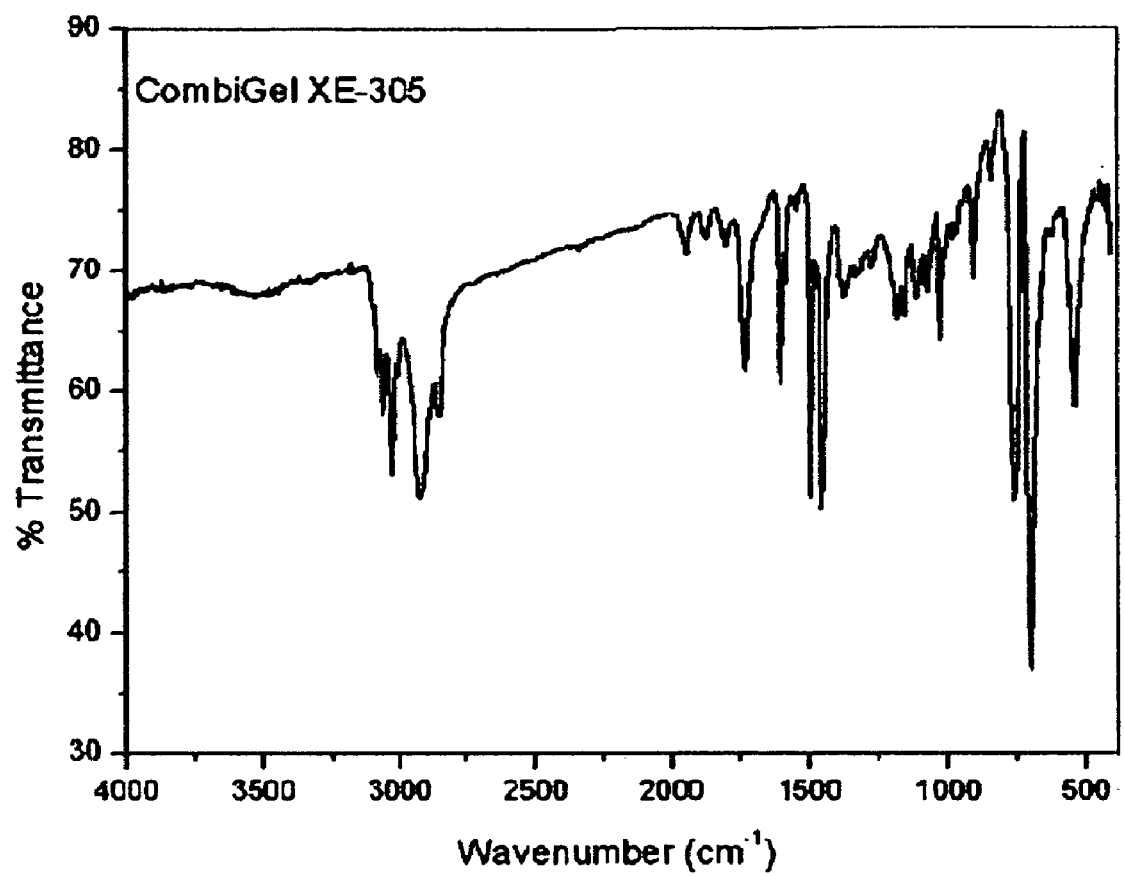
FIG. 7 is the FT-IR spectrum of CombiGel XE-305.
Figure 8:
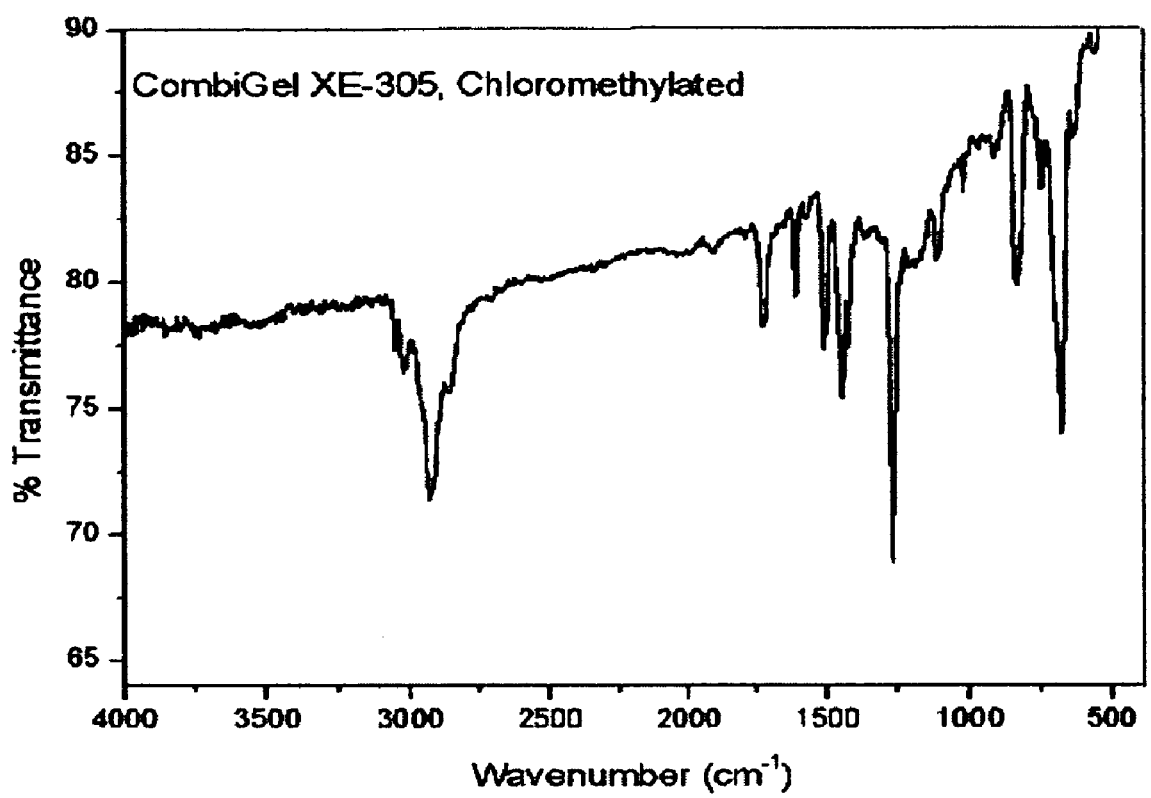
FIG. 8 is the FT-IR spectrum of chloromethylated CombiGel XE-305.

Comparing the IR spectrum of CombiGel XE-305 in FIG. 7 and the IR spectrum of chloromethylated CombiGel XE-305 in FIG. 8, an absorption peak near 1265 cm$^{-1}$, not seen in the IR spectrum of FIG. 7, appears in the IR spectrum of FIG. 8. The absorption peak near 1265 cm$^{-1}$ corresponds to —C—Cl.

The results of the IR spectrum of the chloromethylated polystyrene in FIG. 8 are as follows.

IR spectrum: 2928, 1725, 1612, 1510, 1445, 1422, 1265 cm$^{-1}$.

(2) Immobilization of Dithiol onto Chloromethylated Polystyrene (Cross-Linked with 1% Divinylbenzene)

Figure 6:
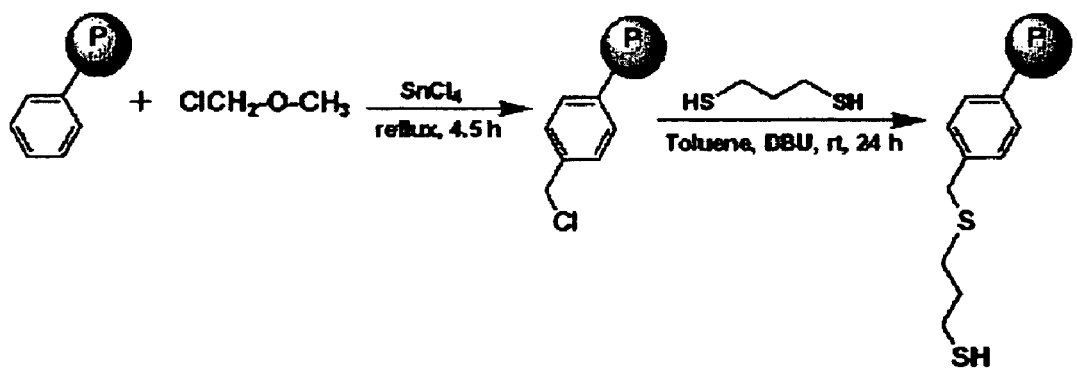
FIG. 6 illustrates the chloromethylation and dithiol reaction of CombiGel XE-305.

2.0 g of the chloromethylated polystyrene (cross-linked with 1% divinylbenzene) obtained in (1) was swelled with 20 mL of toluene. Propane-1,3-dithiol (2 mL, 20 mmol) was added and gently shaken for 15 minutes. 1,8-diazabicyclo [5.4.0]undec-7-ene (DBU) (0.9 mL, 6 mmol) was dropwise added into the reaction mixture and stirred at room temperature for 24 hours (FIG. 6). The resulting resin was filtered under reduced pressure and washed with dimethylformamide (DMF) and then CH$_2$Cl$_2$. The washed resin was dried in a vacuum for 12 hours to immobilize dithiol onto the chloromethylated CombiGel XE-305. As a result of an element analysis, the degree of immobilization of thiol groups was 1.9 mmol/g (per 1 g of the solid phase).

IR spectrum: 2918, 2850, 2563, 1727, 1509, 1423, 1238 cm$^{-1}$

Figure 9:
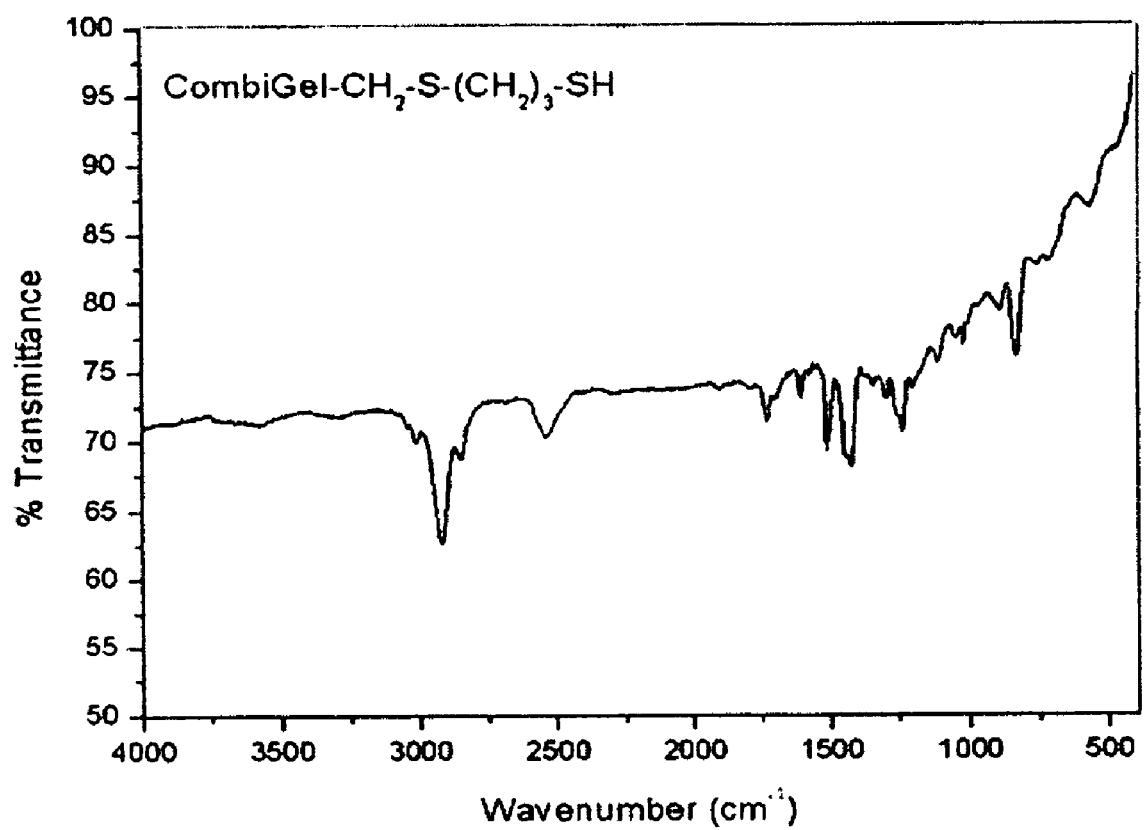
FIG. 9 is the FT-IR spectrum of dithiol-immobilized, chloromethylated CombiGel XE-305.

Referring to the IR spectrum of FIG. 9, a stretching peak of —SH appears near 2563 cm$^{-1}$.

EXAMPLE 7

Figure 10:
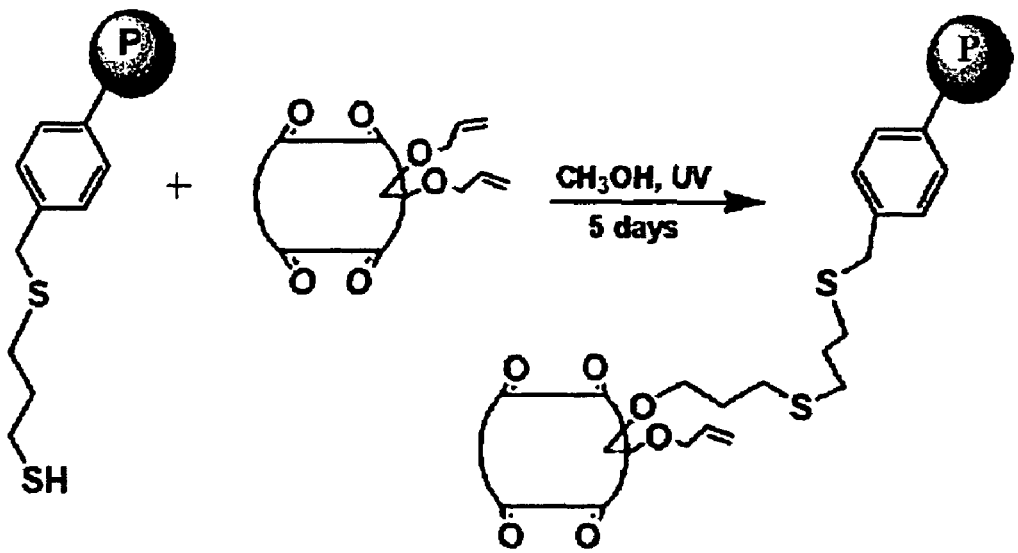
FIG. 10 illustrates the reaction of immobilizing alloyloxycucurbit[7]uril onto CombiGel XE-305 that has undergone chloromethylation and dithiol reaction.

Immobilization of Allyloxycucurbit[7]uril onto Solid Phase 1.5 g of the dithiol-immobilized polystyrene (cross-linked with 1% divinylbenzene) obtained in Example 6 and 1.1 g (0.68 mmol) of allyloxycucurbit[7]uril obtained in Example 3 were added to 16 mL of methanol and irradiated with 300 nm UV rays in an argon environment for 120 hours (5 days) (refer to FIG. 10). After termination of the reaction, the allyloxycucurbit[7]uril-bound polymer resin was filtered under reduced pressure, washed with methanol, chloroform, acetone, and then ether, and dried in a vacuum for 12 hours.

IR Spectrum: 2917, 2852, 1753, 1725, 1510, 1425, 1238 cm$^{-1}$.

A peak of carbonyl groups in cucurbit[7]uril appeared near 1753 cm$^{-1}$ in the IR spectrum. As a result of an element analysis, it was confirmed that 80-115 μmol of allyloxycucurbit[7]uril per 1 g of the solid phase was immobilized.

EXAMPLE 8

Binding of Ligand (Ferrocene Derivative) and Protein (Bovine Serum Albumin)

(1) Synthesis of (N-(ferrocenylmethyl)-6-aminocaproic acid (Fc-aca)

Figure 11:
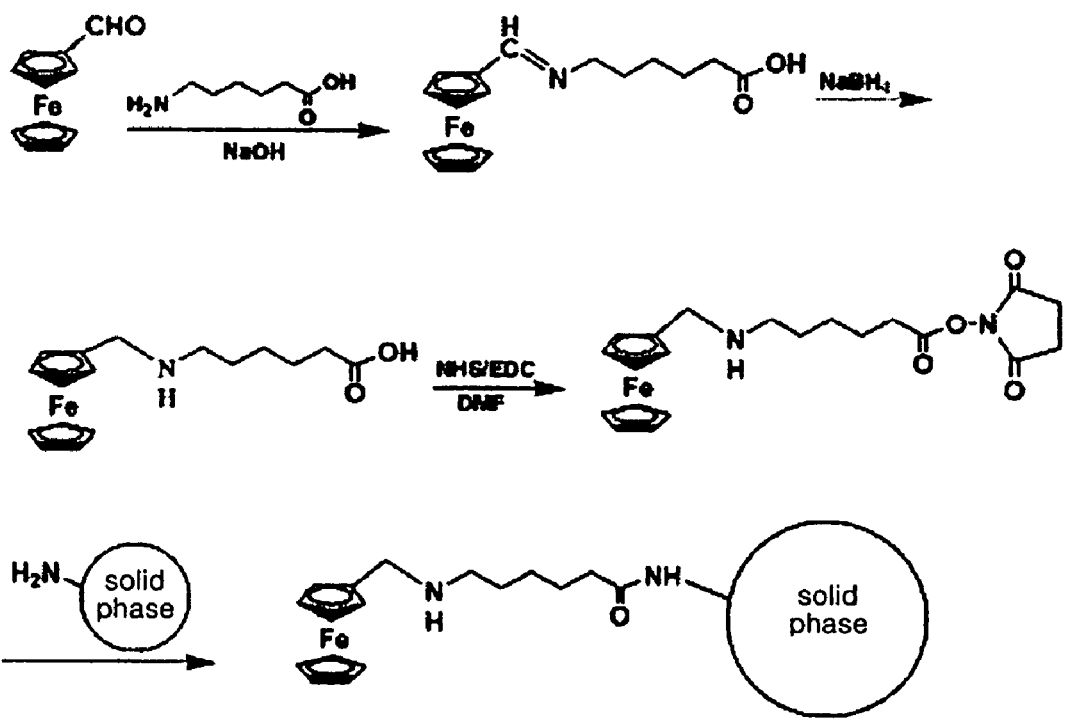
FIG. 11 illustrates the reaction of binding of a solid phase to ferrocene.

After 1.38 g (6.4 mmol) of ferrocene-aldehyde (Aldrich Corp) was dissolved in 20 mL of a DMF solution, the mixture was mixed with a solution of 0.75 g (5.7 mmol) of 6-amino caproic acid (Merck Corp.) in 5 mL of NaOH and refluxed at 80° C. for 2 hours. The reaction mixture was cooled to room temperature, and a solution of NaBH$_4$ (0.63 g, 16.5 mmol) in 5 mL of water was added little by little into the reaction mixture (refer to FIG. 11). After 12 hours later, an aqueous acetic acid solution (10%) was slowly added until the pH reached 5. The reaction by-product ferrocene-CH$_2$OH and unreacted 6-amino caproic acid dissolved in the organic phase was removed through extraction using ethylacetate. The aqueous phase was distilled at 50° C. under reduced pressure to obtain yellowish brown crystals. The yellowish brown crystals were recrystallized by dissolving the crystals in high-temperature ethanol to obtain planar, yellow crystalline N-(ferrocenyl methyl)-6-amino caproic acid.

The N-(ferrocenyl methyl)-6-amino caproic acid was identified through HPLC, $^1$H-NMR, and mass analysis. The recrystallized product was separated with a high purity through HPLC. The $^1$H-NMR spectrum of N-(ferrocenyl methyl)-6-amino caproic acid is as follows.

$^1$H-NMR (D$_2$O, 300 MHz): δ=4.05-4.43 (9H, m, ferrocene ring protons), 3.46 (2H, s, CH$_2$), 2.49 (2H, t, CH$_2$), 1.36 (6H, m, CH$_2$), 2.02 (2H,t CH$_2$).

As a result of a mass analysis, a molecular peak at m/e=330 (Fc-acaH$^+$) appeared.

(2) Binding of N-(ferrocenyl methyl)-6-amino caproic acid (Fc-aca) and bovine serum albumin (BSA)

15 mg of the N-(ferrocenyl methyl)-6-amino caproic acid (Fc-aca) obtained in (1), 6 mg of N-hydrosucciinimide (NHS, Fluka Corp.), and 9 mg of N-(3-dimethylaminopropyl)-N-ethylcarbodiimide hydrochloride (EDC, Fluka Corp.) were dissolved in 0.3 mL of an anhydrous DMF solution. After the temperature was raised to 90° C. in a nitrogen atmosphere, the mixture was stirred for 30 minutes (refer to FIG. 11). The reaction was further performed for 30 minutes while the temperature of the solution was maintained at 80° C. Next, the temperature was cooled to room temperature. 30 µL of the reaction mixture was added into a solution of 7 mg of bovine serum albumin in 1 mL of phosphate buffer solution (100 mM) at 2-minute intervals. The mixture was shaken at room temperature for a day and centrifuged to separate a precipitate. The filtrate was dialyzed in a 50 mM phosphate buffer solution (pH 7.4) for 30 hours to obtain a N-(ferrocenyl methyl)-6-amino caproic acid (Fc-aca)-bound bovine serum albumin (ferrocene-bound BSA).

EXAMPLE 9

Purification of Protein

The ferrocene derivative-bound BSA was purified using the hydroxycucurbit[7]uril-bound solid phase obtained in Example 5.

1.5 g of the hydroxycucurbit[7]uril-immobilized solid phase obtained in Example 5 was put into a 10-mL disposable syringe, and 40 mL of $CH_2Cl_2$ was continuously flowed at a rate of 1.3 mL/min. Next, the solid phase was washed with 50 mL of DMF at a rate of 0.7 mL/min.

2 mg of the ferrocene derivative-bound BSA obtained in Example 8, 1 mg of a glucose oxidase, and 1 mg of a lipase were dissolved in a 0.1 M HEPES buffer solution (pH 6.0) to obtain a protein mixture.

Next, after the protein mixture was slowly flowed into the disposable syringe at a rate of 0.7 mL/min, the syringe was washed with 50 mL of water at a rate of 2 mL/min and then DMF/TEA (40 mL/20 mL) at a rate of 2 mL/min.

Next, 60 mL of a HEPES buffer solution (0.1M, pH 8.5) was flowed at a rate of 2 mL/min to recover an eluate from the syringe.

After the recovered eluate was processed at 60° C. to denaturize protein, Coomassie blue was added into 150 µL of the eluate, loaded onto a SDS-PAGE, and subjected to electrophoresis at 10 mA for 5 hours. At this time, molecular weight markers were simultaneously loaded onto the SDS-PAGE.

Next, the SDS-PAGE gel was separated from the electrophoretic apparatus, washed, dipped in Coomassie blue for 1 hour, and washed with a washing solution overnight.

Figure 12:
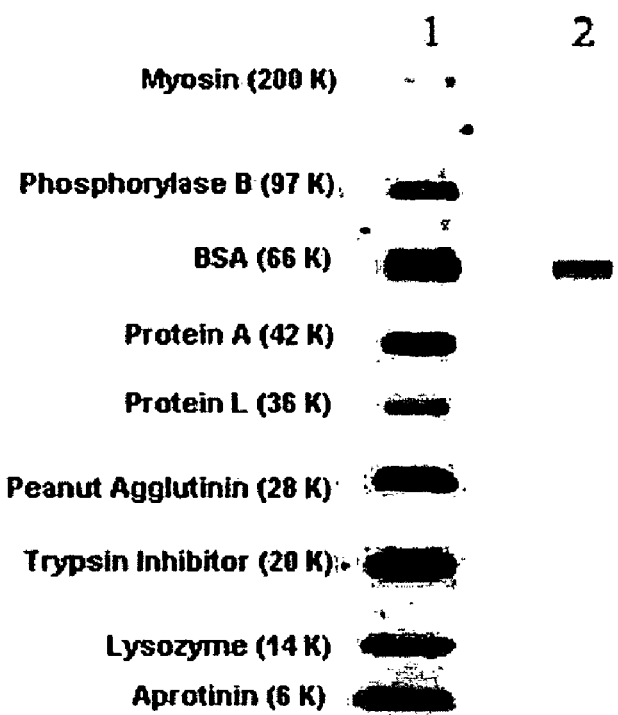
FIG. 12 is the results of electrophoresis on BSA protein purified using a complex (A) of a hydroxycucurbit[7]uril-bound solid support and ferrocene-bound anti-BSA antibody and a complex (B) of allyloxycucurbit[7]uril-bound solid support and ferrocene-bound anti-BSA antibody.
Figure 12:
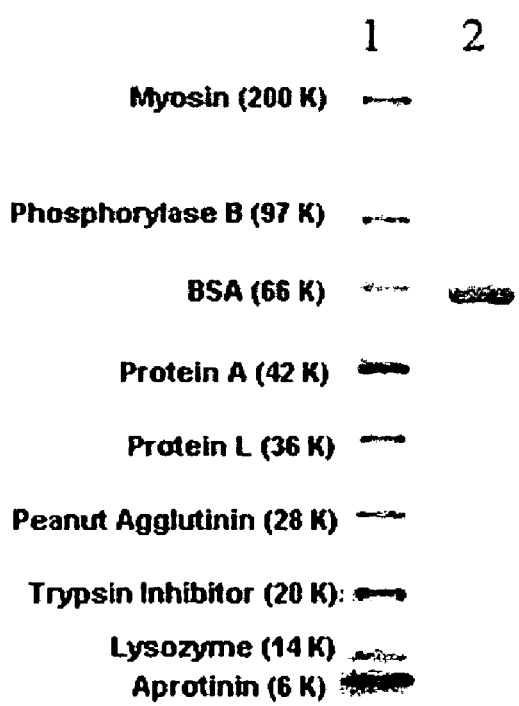

The degree of staining of the gel was measured using a gel scanner. The results are shown in A of FIG. 12. Lane 1 in A of FIG. 12 represents molecular weight markers, and Lane 2 is the results of staining obtained by loading the eluate.

As a result, a single band of 66 kDa appears in Lane 2, indicating that the hydroxycucurbituril-immobilized solid phase can separate and purify ferrocene-bound BSA from the protein mixture.

The eluate was freeze-dried to obtain a pure ferrocene derivative-bound BSA protein.

EXAMPLE 10

Purification of Protein

In this example, a cucurbituril-conjugated protein was purified using a ferrocene-bound solid phase.

(1) Ferrocene Methylamination of Chloromethylated Solid Phase 1.5 g of chloromethylated Combigel XE-305 obtained in (1) of Example 6 was swelled in 14 mL of DMF for 2 hours. The chloromethylated Combigel XE-305 in DMF was added into a DMF-pyridine (1:2 v/v, 9.0 mL) solution in which ferrocene methylamine (1.35 g, 6.3 mmol) was dissolved and stirred at 55° C. for 43 hours. The reaction mixture was filtered under reduced pressure, and the filter cake was washed with solvents, i.e., DMF, CH2Cl2, methanol, and then ether, and dried in a vacuum to obtain a ferrocene-methylaminated Combigel XE-305.

Element Analysis: C, 64.52; H, 6.72, N, 5.10%

The results of the element analysis indicate that 3.64 mmol of ferrocene was bound to 1 g of the ferrocene-methylaminated CombiGel XE-305 polymer.

FT-IR: 3419, 3020, 2936, 1627, 1485, 1210, 1151, 1025 cm$^{-1}$ (2) Synthesis of [3-(2-carboxyethylsulfanyl)propyl-O]$_{14}$ cucurbit[7]uril 2 mL of DMF was put into a quartz tube. Allyloxycucurbit[7]uril ((aryl-O) 14-CB[7], 35 mg, 0.018 mmol) and 3-mercaptopropionic acid (70 mL, 0.78 mmol) were added and reacted under UV irradiation (254 nm) for 36 hours. Next, DMF was removed through distillation under reduced pressure. The reaction mixture was washed four times with 15 mL of diethylether and dried under reduced pressure to obtain 37 mg of [3-(2-carboxyethylsulfanyl)propyl-O]$_{14}$ cucurbit[7]uril with a yield of 60%.

The results of an analysis on the obtained [3-(2-carboxyethyl sulfanyl)propyl-O]14cucurbit[7]uril are as follows.

$^1$H NMR (300 MHz, DMSO-d$_6$): δ=5.56 (d, J=14.3 Hz, 14H), 4.05 (d, J=14.3 Hz, 14H), 3.52 (m, 28H), 2.62 (m, 56H), 2.48 (m, 28H), 1.84 (t, 28H);

$^{13}$C NMR (75 MHz, DMSO): δ=170.0, 151.8, 95.5, 63.2, 40.8, 34.4, 29.2, 26.2; MS (MALDI-TOF): m/z 3454.1 [M+Na$^+$].

(3) Binding of Cucurbit[7]uril Derivative and Bovine Serum Albumin (BSA)

37 mg of [3-(2-carboxyethyl sulfanyl)propyl-O]$_{14}$ cucurbit[7]uril obtained in (2), 6 mg of N-hydrosuccinimide (NHS, Fluka Corp.) and 9 mg of N-(3-dimethylaminopropyl)-N-ethylcarbodiimide hydrochloride (EDC, Fluka Corp.) were dissolved in 0.3 mL of an anhydrous DMF solution and stirred for 30 minutes after the temperature was raised to 90☐ in a nitrogen atmosphere.

The reaction was further performed for 30 minutes while the temperature of the solution was maintained at 80 ☐. 30 µL of the reaction mixture was added into a solution of 7 mg of bovine serum albumin (BSA, Sigma Corp.) in 1 mL of a phosphate buffer solution (100 mM) at 2-minute intervals. The mixture was shaken at room temperature for a day and centrifuged to separate a precipitate. The filtrate was dialyzed in a 50 mM phosphate buffer solution (pH 7.4) for 30 hours to obtain a 3-(2-carboxyethylsulfanyl)propyl-O]$_{14}$ cucurbit[7]uril-bound bovine serum albumin. The cucurbit[7]uril-conjugated BSA was purified using the ferrocene-methylaminated solid phase obtained in (1).

1.5 g of the ferrocene-methylaminated solid phase was put into a 10-mL disposable syringe, and 40 mL of $CH_2Cl_2$ was continuously flowed at a rate of 1.3 mL/min. Next, the resin was washed with 50 mL of DMF at a flow rate of 0.7 mL/min.

2 mg of the cucurbit[7]uril-bound BSA, 1 mg of glucose oxidase, and 1 mg of lipase were dissolved in a phosphate buffer solution (0.1M, pH 6.0) to obtain a protein mixture.

Next, after the protein mixture was slowly flowed through a column at a rate of 0.7 mL/min, the syringe was washed with 50 mL of water at a flow rate of 2 mL/min and then DMF/TEA (40 mL/20 mL) at a flow rate of 2 mL/min.

Next, 60 mL of a HEPES buffer solution (0.1M, pH 8.5) was flowed at a rate of 2 mL/min to recover an eluate from the syringe. After the recovered eluate was processed at 60° C. to denaturize protein, Coomassie blue was added into 150 µL of the eluate, loaded onto a SDS-PAGE, and subjected to electrophoresis at 10 mA for 5 hours. At this time, molecular weight markers were simultaneously loaded onto the SDS-PAGE.

The degree of staining of the gel was measured using a gel scanner. The results are shown in B of FIG. 12. Lane 1 in B of FIG. 12 represents molecular weight markers, and Lane 2 is the results of staining obtained by loading the eluate.

As a result, a single band of 66 kDa appears in Lane 2, indicating that the ferrocene-bound solid phase can separate and purify cucurbituril derivative-bound BSA from the protein mixture.

The eluate was freeze-dried to obtain a cucurbituril derivative-bound BSA protein.

EXAMPLE 11

Purification of Antigen

In this example, an antigen that specifically binds to an antibody was purified using the allyloxycucurbit[7]uril-conjugated solid phase obtained in Example 7 and a ferrocene derivative-conjugated antibody.

(1) Preparation of Cucurbituril Derivative-Bound Solid Phase 300 mg of the allyloxycucurbit[7]uril-bound solid phase obtained in Example 7 in an excess of HEPES solution (50 mM, pH 8.5) was centrifuged at 10,000 rpm for 5 minutes. The supernatant was removed using a 200-µL pipette, and the remaining solid phase was washed twice.

(2) Preparation of Ferrocene Derivative-Bound Anti-BSA Protein Solution

A ferrocene derivative-bound anti-BSA protein solution was prepared as follows.

15 mg of the N-(ferrocenyl methyl)-6-amino caproic acid (Fc-aca) obtained in (1) of Example 8, 6 mg of N-hydrosuccinimide (NHS, Fluka Corp.), and 9 mg of N-(3-dimethylaminopropyl)-N-ethylcarbodiimide hydrochloride (EDC, Fluka Corp.) were dissolved in 0.3 mL of an anhydrous DMF solution, and stirred for 30 minutes after the temperature was raised to 90° C. in a nitrogen atmosphere. The reaction was further performed for 30 minutes while the temperature of the solution was maintained at 80° C. Then, the temperature of the solution was cooled to room temperature. 30 µL of the reaction mixture was added into a solution of 7 mg of an anti-BSA solution (Sigma Co.) in 1 mL of a phosphate buffer solution (100 mM) at 2-minute intervals. The mixture was shaken at room temperature for a day and centrifuged to separate a precipitate. The filtrate was dialyzed in a 50-mM phosphate buffer solution (pH 7.4) for 30 hours to obtain an anti-BSA conjugated with N-(ferrocenyl methyl)-6-amino caproic acid (Fc-aca) (ferrocene-conjugated BSA).

A solution of an anti-body protein of the ferrocene-conjugated anti-BSA was diluted with 50 mM of HEPES (pH 7.4) to a concentration of 100 µg/mL and a volume of 500 µL. (The antibody protein solution was subjected to dialysis or gel filtration chromatography before use to remove external proteins or other samples including azide, glycine, TRIS, and primary amine groups)

(3) Binding of the Allyloxycucurbit[7]uril-Bound Solid Phase and Ferrocene Derivative-Bound Anti-BSA Protein The allyloxycucurbit[7]uril-bound solid phase prepared in (1) was suspended in 500 µL of HEPES solution (50 mM, pH 7.4). 500 µL of the solution of the antibody of the ferrocene-bound anti-BSA, which was diluted to 100 µg/mL in (2), was added into the suspension.

The mixed solution was slowly stirred at room temperature in a dark room for 3 hours. Next, particles were washed twice with a HEPES buffer solution (pH 7.4). Next, 500 µL of a blocking buffer solution (0.1 M ethanol amine and HEPES buffer solution) was added. Next, the solid phase was washed twice with 500 µL of the HEPES buffer solution (pH 7.4).

(4) Purification of Antigen

A complex of the ferrocene derivative-bound anti-BSA protein and the allyloxycucurbit[7]uril-bound solid phase was put into two tubes. 500 µL of a buffer solution containing lysozyme (1 mg/mL) was added into one of the two tubes as a control group, and 500 µL of a buffer solution containing BSA (1 mg/mL) was added into the other tube.

The tubes each containing the solid phase and one of the protein solutions were slowly stirred at room temperature in a dark room for 3 hours. Solid phase particles were washed twice with a HEPES buffer solution (pH 7.4).

A solid support treated with the buffer solution containing lysozyme as a control group and a solid support treated with the buffer solution containing BSA were extracted using 300 µL of an elution buffer solution (0.1 M glycine).

After the protein was denaturized at a temperature of 60° C. or less, Coomassie blue was added into 150 µL of the elution solution, loaded onto an SDS-PAGE, and subjected to electrophoresis at 10 mA for 5 hours. At this time, molecular weight markers were also loaded onto the SDS-PAGE.

Next, the SDS-PAGE gel was separated from the electrophoretic apparatus, washed, dipped in Coomassie blue for 1 hour, and washed with a washing solution overnight.

Figures 13, 14:
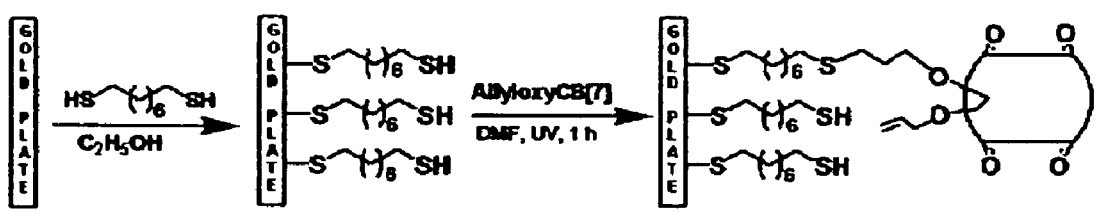
FIG. 13 is the results of electrophoresis on a lysozyme-containing protein solution (Lane 2) and a BSA-containing protein solution (Lane 3) purified using a complex of allyloxycucurbituril-bound solid phase and ferrocene-bound anti-BSA, in which Lane 1 indicates molecular weight markers.
FIG. 14 illustrates the reaction of immobilization of allyloxycucurbit[7]uril on a gold surface.

The degree of staining of the gel was measured using a gel scanner. The results are shown in FIG. 13. Lane 1 in FIG. 13 represents molecular weight markers, and Lanes 2 and 3 are the results of staining obtained by loading the lysozyme-containing solution and the BSA-containing solution, respectively.

Referring to FIG. 13, in the solid support treated with the lysozyme-containing solution (Lane 2), no protein was detected. In the solid support treated with the BSA-containing solution (Lane 3), a bank of 66 kDa appeared, indicating that BSA can be separated using the complex of the cucurbituril-bound solid phase and the ferrocene derivative-bound anti-BSA.

EXAMPLE 12

Sensor Chip (1) Immobilization of Allyloxycucurbit[7]uril onto Gold Surface

A flat gold electrode (2 cm×1 cm) was dipped in an ethanol solution containing 1 mM of 1,8-octanedithiol for 2 hours to immobilize thiol groups onto a surface of the gold substrate. The gold substrate was dipped in a DMF solution in which the allyloxycucurbit[7]uril (1 mM) prepared in Example 3 had been dissolved, and irradiated with UV of 254 nm and 300 nm for 1 hour. The gold substrate was drawn out of the DMF solution and washed with DMF to obtain the gold electrode to which the allyloxycucurbit[7]uril was covalently bound (refer to FIG. 14).

(2) Inclusion of Ferrocene Molecules into Allyloxycucurbit[7]uril Immobilized on Gold Surface In the present example, it was confirmed whether ferrocene molecules could be included into cavities in the allyloxycucurbit[7]uril.

Figure 15:
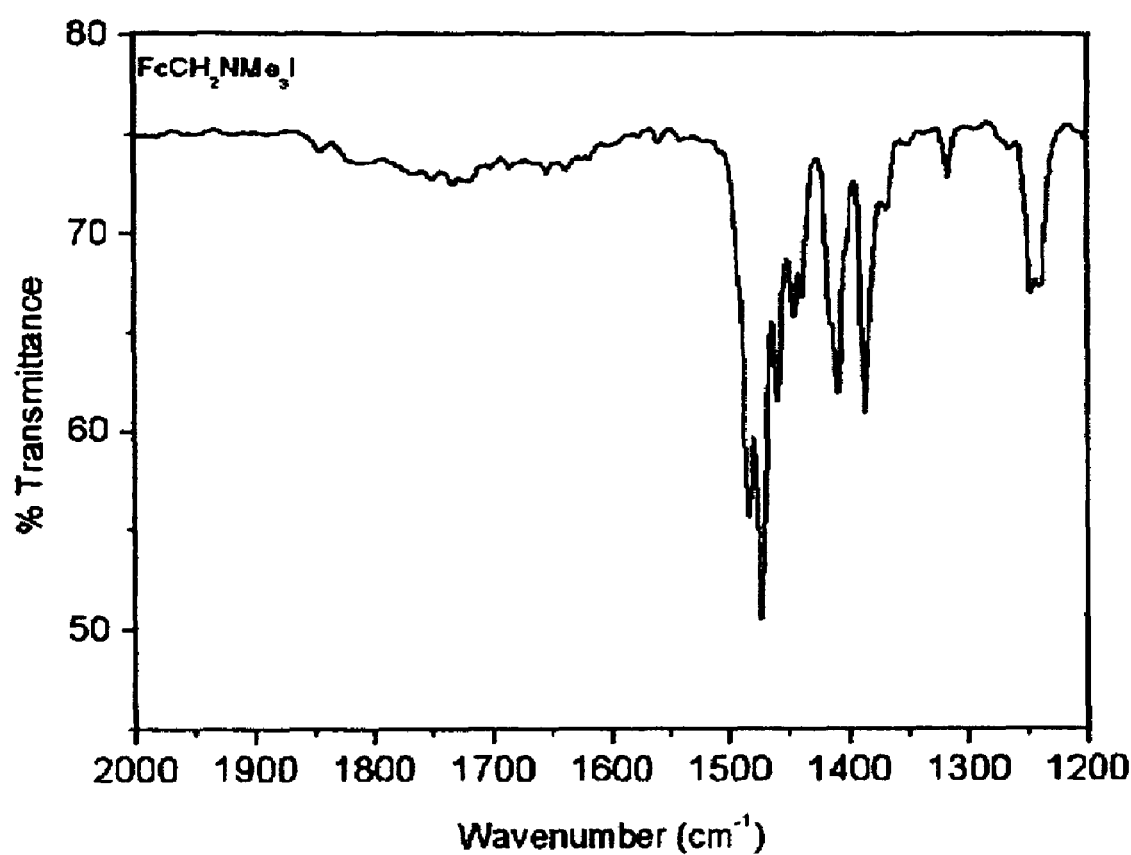
FIG. 15 is the FT-IR spectrum of ferrocene methylene trimethylammonium iodide.
Figure 16:
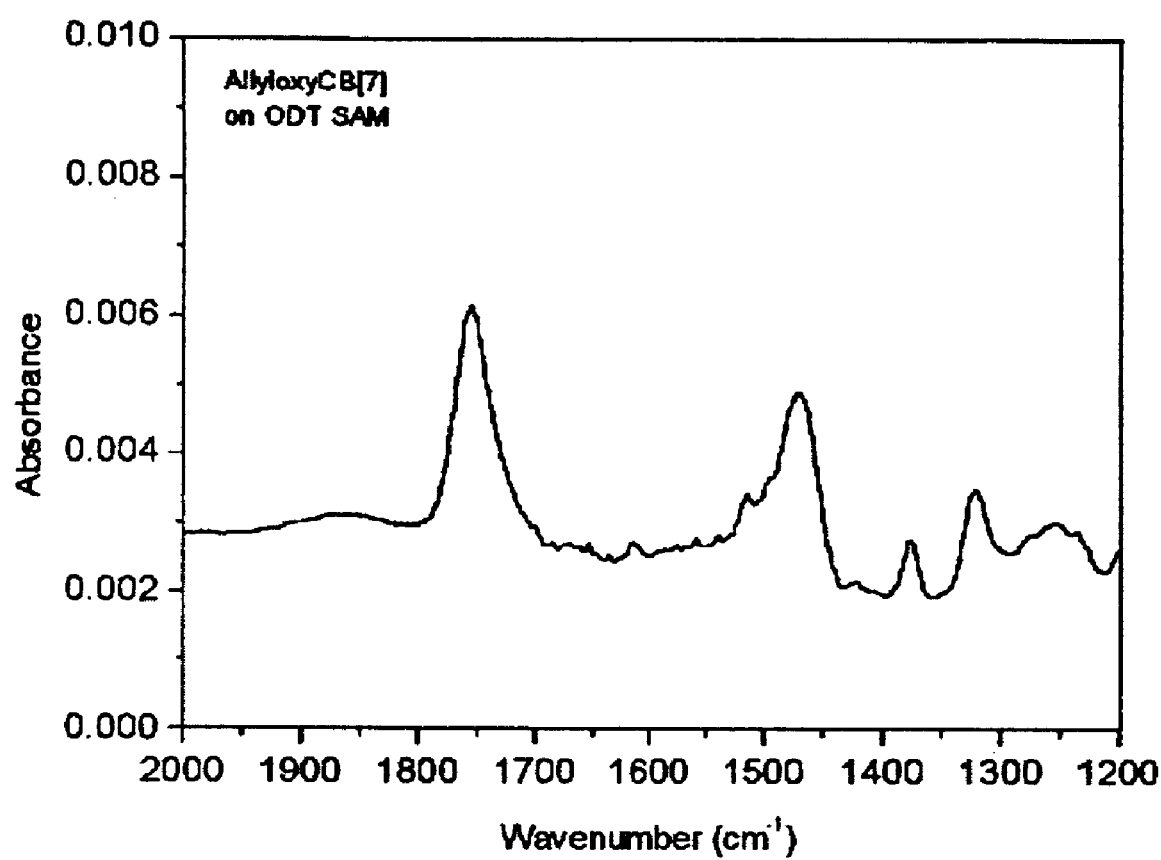
FIG. 16 is the FT-IR spectrum of allyloxycucurbit[7]uril bound to a surface of a gold electrode.

Initially, the gold electrode to which the allyloxycucurbit[7]uril was covalently bound in (a) was dipped in a 0.2M ferrocene trimethylammonium iodide solution (pH 6.2) for 1 hour. In addition, the inclusion of ferrocene trimethylammonium iodide into the cavities of allyloxycucurbit[7]uril was confirmed through a Fourier-transform infrared absorption experiment (refer to FIGS. 15 and 16).

Figure 17:
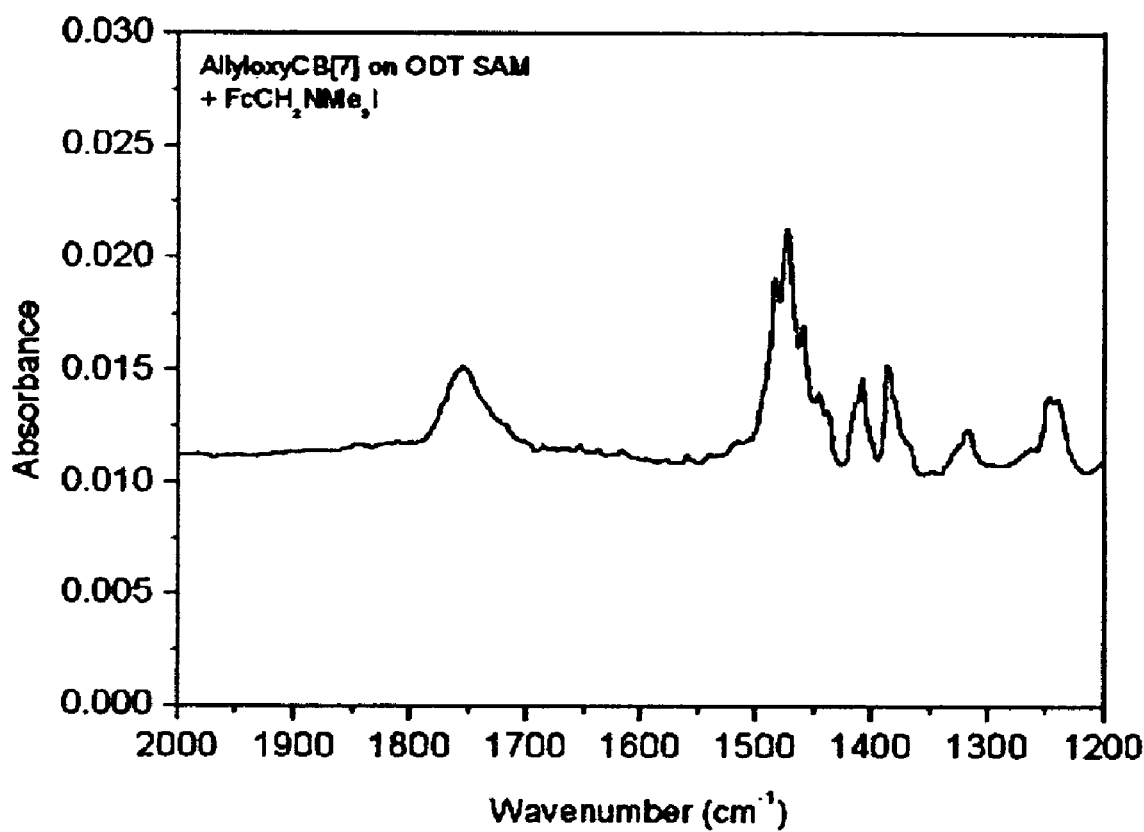
FIG. 17 is the FT-IR spectrum of ferrocene methylene trimethyl ammonium iodide trapped in allyloxycucurbituril [7] molecules bound to the surface of the gold electrode.

FTIR spectrum of ferrocene trimethyl ammonium iodide (refer to FIG. 15): 1483, 1473, 1459, 1445, 1409, 1386, 1247 cm−1;

FTIR spectrum of the allyloxycucurbit[7]uril (refer to FIG. 16): 1756, 1471, 1377, 1322, 1255 cm−1;

FTIR spectrum of the reaction product between the gold electrode to which the allyloxycucurbit[7]uril was covalently bound and ferrocene trimethylammonium iodide (refer to FIG. 17): 1755, 1483, 1473, 1459, 1409, 1386, 1317, 1247 cm−1

(3) Inclusion of Ferrocene-Bound Glucose Oxidase into Allyloxycucurbit[7]uril Immobilized on Gold Surface and Enzymetic Activity Measurement An enzyme solution of ferrocene-bound glucose oxidase (Fc-GOx) was prepared in the same manner as in (2) of Example 8, except that a glucose oxidase, instead of BSA, was used.

Figure 18:
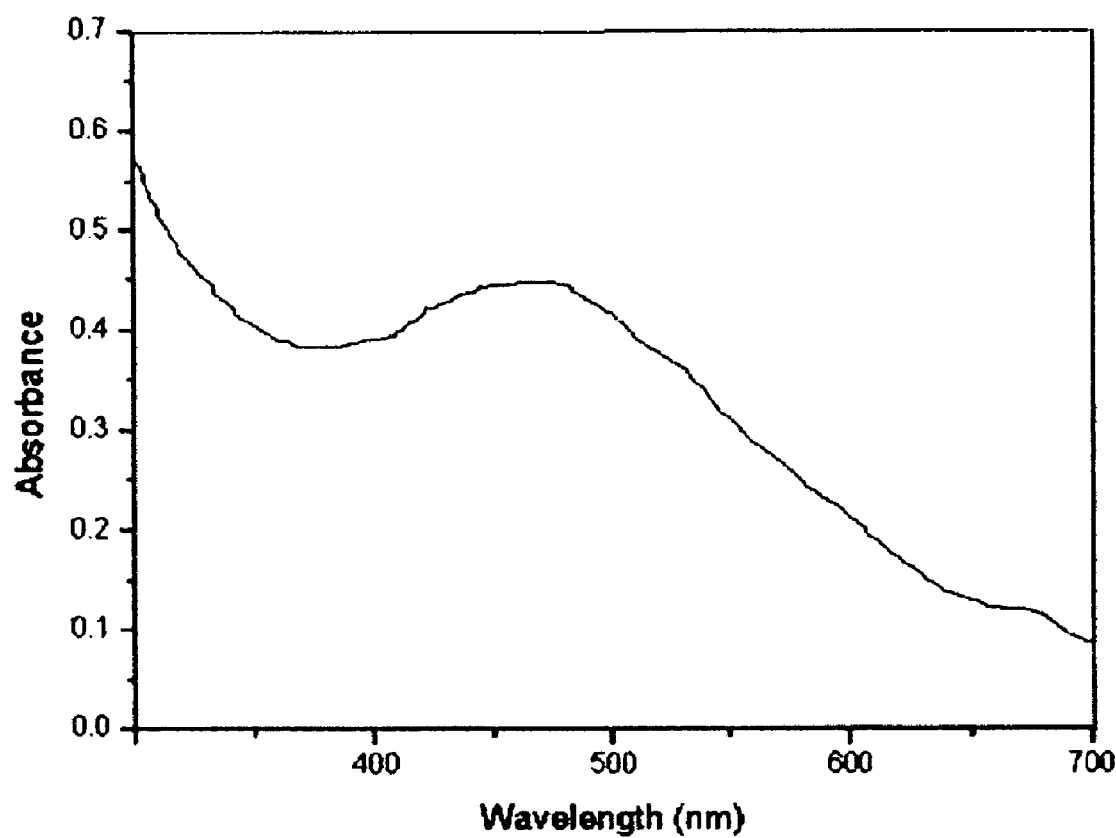
FIG. 18 is the UV-Vis absorption spectrum of o-dianisidine. 2HCl showing the activity of a sensor in which a glucose oxidase is bound to cucurbit[7]uril and ferrocene.

Next, a gold electrode to which the allyloxycucurbit[7]uril was immobilized on its surface in (1) was dipped in a 0.1 M phosphate buffer solution (200 Uml-1-glucose oxidase, pH 6.3) containing 10 mL of the enzyme solution of ferrocene-bound glucose oxidase (Fc-GOx) at room temperature for 30 minutes. The gold electrode was drawn out of the phosphate buffer solution and washed with 0.1M phosphate buffer solution (pH 6.3). The activity of the glucose oxidase included into the allyloxycucurbit[7]uril was measured after the gold electrode was dipped in 0.1M glucose solution (10 mL of 0.1 M phosphate buffer solution, pH 6) at 25° C. for 1 minute to culture the enzyme. After the gold electrode was removed from the glucose solution, 100 μl of a peroxidase solution (50 purpurogallin units m1-1) and 20 μl of a o-dianisidine.2HCl solution (1% m/v in water) were added into the glucose solution, and the mixed solution was poured into a glass cell. The enzymetic activity was measured as the absorbance at 460 nm (refer to FIG. 18).

The absorbance of light at 460 nm signifies the activity of glucose oxidase. In particular, hydrogen peroxide is generated as a result of the reaction between glucose and the glucose oxidase. As peroxidase reacts with the hydrogen peroxide and oxidizes o-dianisidine.2HCl, light absorption occurs at 460 nm. Accordingly, the activity of the enzyme can be measured as the absorbance of light at 460 nm.

(4) Electrochemical Measurement

To measure the glucose concentration of a sample, the amount of $H_2O_2$, which is a product from the enzymetic reaction on glucose, was measured. The gold electrode manufactured in (1) was used to measure the concentration of $H_2O_2$. The glucose oxidase was dissolved in a 0.1-M phosphate buffer solution to a concentration of 10-120 mM. Every experiment was performed in a 25° C.-incubator.

Figure 19:
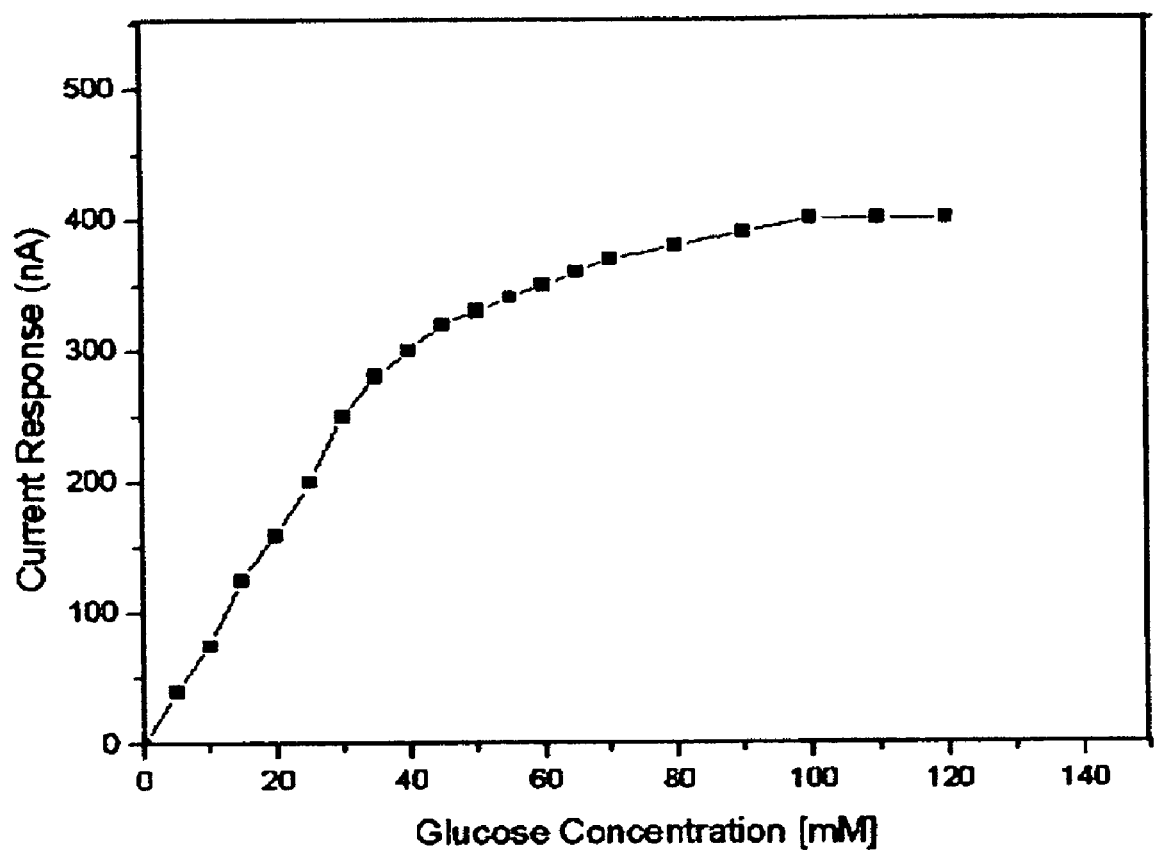
FIG. 19 is a calibration curve of glucose concentration in a range of 10-120 mM obtained using the sensor in which the glucose oxidase is bound to cucurbit[7]uril and ferrocene.

A calibration curve was obtained based on the results of the experiments (refer to FIG. 19).

EXAMPLE 13

Solid Catalyst (1) Preparation of N-(ferrocenyl methyl)-6-amino caproic acid (Fc-aca)-conjugated lipase 15 mg of the N-(ferrocenyl methyl)-6-amino caproic acid (Fc-aca) prepared in (1) of Example 8, 6 mg of N-hydrosuccinimide (NHS, Fluka Corp), and 9 mg of N-(3-dimethylaminopropyl)-N-ethylcarbodiimide hydrochloride (EDC, Fluka Corp.) were dissolved in 0.3 mL of an anhydrous DMF solution and stirred for 30 minutes after the temperature was raised to 90° C. in a nitrogen atmosphere. The reaction was further performed for 30 minutes while the temperature of the solution was maintained at 80° C. 30 μL of the reaction mixture was added into a solution of 7 mg of lipase in 1 mL of a phosphate buffer solution (100 mM) at 2-minute intervals. The mixture was shaken at room temperature for a day and centrifuged to separate a precipitate. The filtrate was dialyzed in a 50-mM phosphate buffer solution (pH 7.4) for 30 hours to obtain an N-(ferrocenyl methyl)-6-amino caproic acid (Fc-aca)-bound lipase (ferrocene-bound lipase).

(2) Inclusion of Ferrocene-Bound Lipase Particles into Hydroxycucurbit[7]uril Immobilized on Solid Support 1.0 g of the hydroxycucurbit[7]uril immobilized on the polymer resin in Example 6 was put into a 10-mL disposable syringe, and 40 mL of $CH_2Cl_2$ was continuously flowed at a rate of 1.3 mL/min. Next, the resin was washed with 50 mL of DMF at a rate of 0.7 mL/min. 2 mg of the ferrocene-bound lipase obtained in (1) was dissolved in a phosphate buffer solution (0.1M, pH 7.4) and slowly flowed into a column at a rate of 0.7 mL/min. Next, the syringe was washed with 50 mL of water at a rate of 2 mL/min. Next, polymer particles of the polymer support with the hydroxycucurbit[7]uril immobilized thereon and into which the ferrocene-bound lipase was included in the syringe was collected the syringe and dried in a vacuum.

The resulting polymer resin including the ferrocene-bound lipase particles in the hydroxycucurbit[7]uril immobilized on the solid support was used as a catalyst.

(3) Epoxidation of α-Pinene

After 2.85 mL of α-pinene (15 mmol) and 2.37 mL of octanoic acid (15 mmol) were dissolved in 8 mL of toluene, 150 mg of the catalyst obtained in (2) was added into the solution. The mixture was slowly stirred at room temperature to initiate reaction while gradually adding 2.6 mL of $H_2O_2$ (23 mmol) into the mixture.

After 4 hours later, the reaction mixture was filtered to recover catalyst particles. The filtrate was vaporized under reduced pressure and subjected to column chromatography to separate a product.

The separated α-pinene oxide compound was identified through 1H NMR, 13C NMR, and mass analysis. A portion of the organic phase was sampled at a regular time interval to identify the product.

α-pinene oxide: oil, boiling point: 102-104° C./50 mm:

$^1$H-NMR (CDCl$_3$, 300 MHz): δ=0.91 (3H, s, CH$_3$), 1.30 (3H, s, CH$_3$), 1.32 (3H, s, CH$_3$), 1.59 (1H, m, CH), 1.72 (1H, m, CH), 1.90-2.05 (4H, m, CH$_2$), 3.08 (1H, m, CH);

$^{13}$C-NMR (CDCl$_3$, 300 MHz): δ=60.23, 56.7, 44.9, 40.4, 39.6, 27.64, 26.72, 25.87, 22.41, 20.18. MS (EI) m/z 152 (M$^+$).

(4) Transesterification Between Methylacetoacetate and N-Butanol 2.1 mL of methylacetoacetate (20 mmol) and 1.8 mL of n-butanol (20 mmol) were added into 20 mL of toluene and stirred at 30° C. and 400 rpm for 15 minutes. 155 mg of the catalyst (FerlipaseCB(7) polymer beads) prepared in (2) was added into the mixture to initiate reaction. A clear liquid sample was periodically sampled and analyzed using gas chromatography to identify n-butyl acetoacetate, which was the reaction product.

$^1$H-NMR (CDCl$_3$, 300 MHz): δ=2.12 (3H, s, CH$_3$), 3.46 (2H, s, CH$_2$), 4.05 (2H, t, CH$_2$), 1.53 (2H, m, CH$_2$), 1.35 (2H, m, CH$_2$), 1.06 (3H, t, CH$_3$)

EXAMPLE 14

Measurement of Degree of Cell Death

After a ferrocene derivative bound to annexin V, which is known as a protein that can selectively bind to surfaces of dead cells, was treated on cells induced to die using an anti-cancer drug, the cells were treated with an FITC-bound cucurbituril derivative, and the degree of cell death was measured through flow cytometry.

(1) Induction of Cell Death by the Treatment with Anti-Cancer Drug 2 mL of RPMI-26040 culture solution (containing 10% FCS) and about 106 KB cells (oral carcinoma cells) (obtained from the Korean Cell Line Bank (KCLB)) were cultured in two 6-well cell culture dishes at 37° C. in a 5% CO2 condition for 48 hours.

Next, 2 mL of the RPMT-1640 culture solution (containing: 10% FGS) in one of the 6-well cell culture dishes was replaced by the same, fresh culture solution, and 2 mL of the RPMT-1640 culture solution in the other 6-well cell culture dish was replaced by 0.5 μM (0.3 μg/mL) of doxorubicin, and the two culture dishes were incubated at 37° C. in a 5% CO2 condition for 3 days.

(2) Treatment of Cells with Annexin V-Ferrocene Derivative 15 mg of the N-(ferrocenyl methyl)-6-amino caproic acid (Fc-aca) obtained in (1) of Example 8, 6 mg of N-hydroxysuccinimide (NHS, Fluka Corp.), and 9 mg of N-(3-dimethylaminopropyl)-N-ethylcarbodiimide hydrochloride (EDC, Fluka Corp.) were dissolved in 0.3 mL of an anhydrous DMF solution, and stirred for 30 minutes after the temperature was raised to 90° C. in a nitrogen atmosphere.

The reaction was further performed for 30 minutes while the temperature of the solution was maintained at 80° C. Then, the temperature of the solution was cooled to room temperature. 30 μL of the reaction mixture was added into a solution of 9 mg of annexin V (Sigma Corp.) in 1 mL of a phosphate buffer solution (100 mM) at 2-minute intervals. The mixture was shaken at room temperature for a day and centrifuged to separate a precipitate. The filtrate was dialyzed in a 50-mM phosphate buffer solution (pH 7.4) for 30 hours to obtain an N-(ferrocenyl methyl)-6-amino caproic acid (Fc-aca)-bound annexin V (annexin V-ferrocene derivative).

The culture solution in the two cell culture dishes incubated in (1) was removed. The cell cultures in the dishes were washed twice with 2 mL of a PBS buffer solution (pH 7.4, Sigma Corp.), and then 2 mL of a RPMT-1640 culture solution (including 10% FCS) containing 100 μL of an ferrocene-annexin V reagent (including 10 μL of a 10× binding buffer solution (Trevigen Corp.), 1 μL of ferrocene-annexin V, and 89 μL of distilled water) was added into the culture dishes and incubated at 37° C. in a 5% CO2 condition for 2 hours.

Next, the culture solution was removed from the two cell culture dishes, and each of the cell cultures was washed twice with 2 mL of a PBS buffer (pH 7.4, Sigma Corp.) and dipped in 2 mL of a PBS buffer solution (pH 7.4, Sigma Corp.) containing 2% formaldehyde for 15 minutes to fix the cells.

(3) Preparation of [3-(2-aminoethyl sulfanyl)propyl-O] 14cucurbit[7]uril 3 mL of DMF, 50 mg (0.025 mmol) of the allyloxycucurbit [7]uril obtained in Example 3, 87 mg (0.77 mmol) of 2-aminoethanothiol hydrochloride, and 0.32 mg of AIBN were put into a quartz tube and sealed. The quartz tube was charged with nitrogen using a freeze-pump-thaw degassing method and placed in a reactor under 254 nm-UV radiation for 36 hours. After termination of the reaction, the solvent was removed under reduced pressure, 0.5 mL of triethylamine was added into the quartz tube, and the mixture was washed four times with 15 mL of diethylether. The resulting compound was dried under reduced pressure to obtain 48 mg of a final compound with a yield of 62%.

1H NMR (300 MHz, DMSO): δ=5.56 (d, J=14.3 Hz, 14H), 4.05 (d, J=14.3 Hz, 14H), 3.52 (m, 28H), 2.91 (m, 28H), 2.62 (m, 56H), 1.84 (t, 28H); $^{13}$C NMR (75 MHz, DMSO): δ=151.8, 95.5, 63.2, 40.8, 38.1, 33.4, 32.2 26.2; MS (MALDI-TOF): m/z 3048.1 [M+Na+].

(4) Treatment of FITC-Cucurbituril Derivative 100 mg (0.033 mmol) of [3-(aminoethyl sulfanyl)propyl-O]14 cucurbit[7]uril and 1 mL of 1M NaOH were added into 5 mL of DMSO, and a solution of 28.26 mg (0.072 mmol) of FITC dissolved in 8 mL of DMSO was added into the solution and stirred at room temperature for 12 hours.

10 mL of distilled water was added dropwise into the reaction container to neutralize the reaction solution. The neutralized solution was dialyzed for 12 hours, and the solvent was removed through distillation under reduced pressure to obtain 75 mg of a final product in white solid form with a yield of 60%.

The final product was stored in a 4° C., light-shielded refrigerator.

$^1$H NMR (300 MHz, DMSO): =10.5 (s, 2H), 9.9 (br, 2H), 8.2 (s, 2H), 7.9 (m, 2H), 7.3 (m, 2H), 6.4 6.7 (m, 12H), 5.56 (d, J=14.3 Hz, 14H), 4.05 (d, J=14.3 Hz, 14H), 3.52 (m, 28H), 2.91 (m, 28H), 2.62 (m, 56H), 1.84 (t, 28H).

The buffer solution was removed from the two cell culture dishes, and each of the cell cultures was washed twice with 9 mL of a PBS buffer solution (Simga Corp.) and dipped for 15 minutes in 9 mL of a PBS buffer solution (Sigma Corp.) in which 45 μg of the FITC-cucurbituril derivative obtained above had been dissolved.

(5) Measurement of Degree of Cell Death

The cell samples in the PBS buffer solution were transferred into centrifuge tubes, centrifuged to separate cells, and suspended in 500 μL of a PBS buffer solution.

Next, the degree of cell depth in each of the samples was measured through flow cytometry (FACSCalibur, Becton Dickinson Corp., Ex=488 nm, Em=530 nm (for FITC detection).

Figure 20:
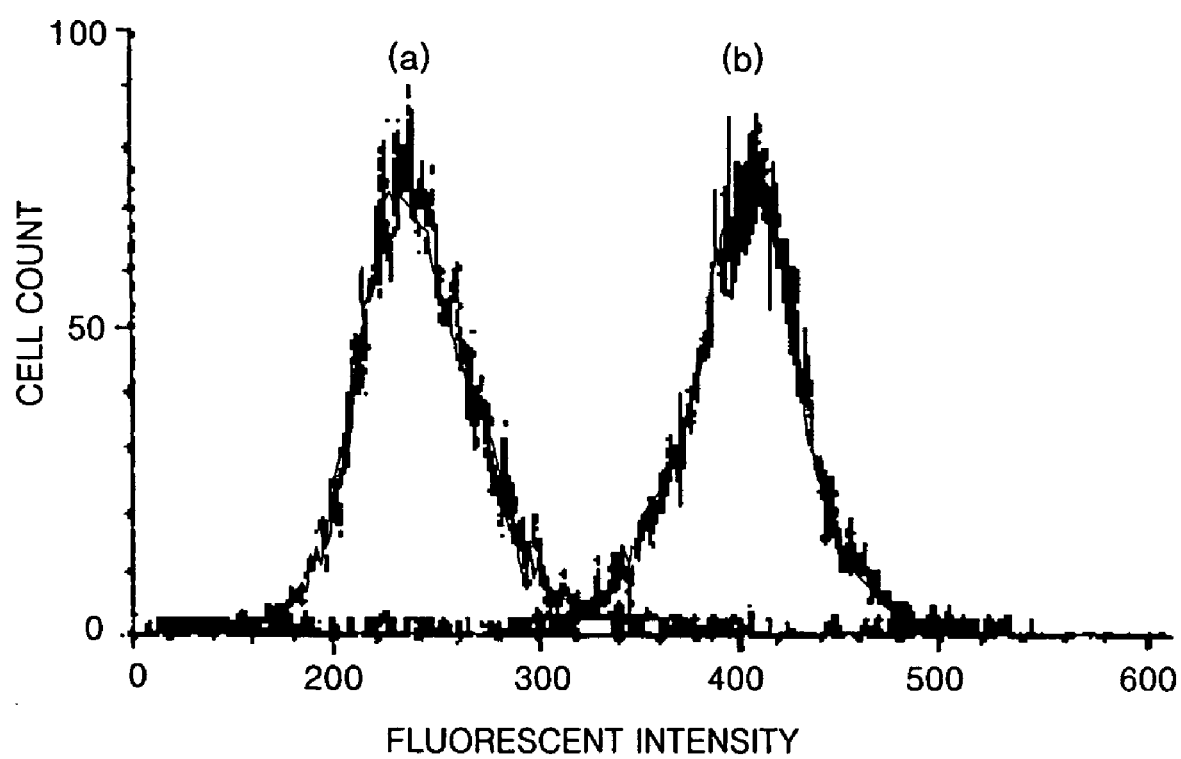
FIG. 20 is the results of flow cytometry showing the fluorescent intensity of fluoresceine isothiocyanate (FITC) in KB cells (a) untreated with doxorubicin and KB cells (b) treated with doxorubicin, both KB cells (a) and (b) being treated with an annexin V-ferrocene derivative and then a FITC-cucurbituril derivative before the flow cymetry.

As a result of the flow cytometry, a greater intensity FITC signal was detected from the sample treated with doxorubicin than the sample not treated with doxorubicin, indicating that most cells in the doxorubicin-treated sample died. In FIG. 20, (a) indicates KB cells not treated with doxorubicin, and (b) indicates KB cells treated with doxorubicin.

EXAMPLE 15

Separation of cucurbit[7]uril using affinity chromatography (1) Adamantylamination of chloromethylated polystyrene 2.0 g of the chloromethylated polystyrene (cross-linked with 1% divinylbenzene) (chloromethylated Combigel XE-305) obtained in (1) of Example 6 was sufficiently dipped in 17 mL of DMF for 2 hours. 1.59 g (8.5 mmol) of 1-adamantaneamine hydrochloride (TCI) was slowly added into 12.0 mL of a DMF-pyridine (1:2 v/v), and the chloromethylated Combigel XE-305 in DMF was added into the solution and stirred at 55° C. for 43 hours. The reaction mixture was filtered with DMF, CH2Cl2, methanol, and then diethylether and washed. The washed reaction mixture was dried in a vacuum to obtain an adamantylaminated CombiGel XE-305.

Element analysis: C, 61.73: H, 6.87, N, 5.43%

(These results confirm that 3.88 mmol of damantylamine was included in 1 g of the adamantylaminated CombiGel XE-305.)

Figure 21:
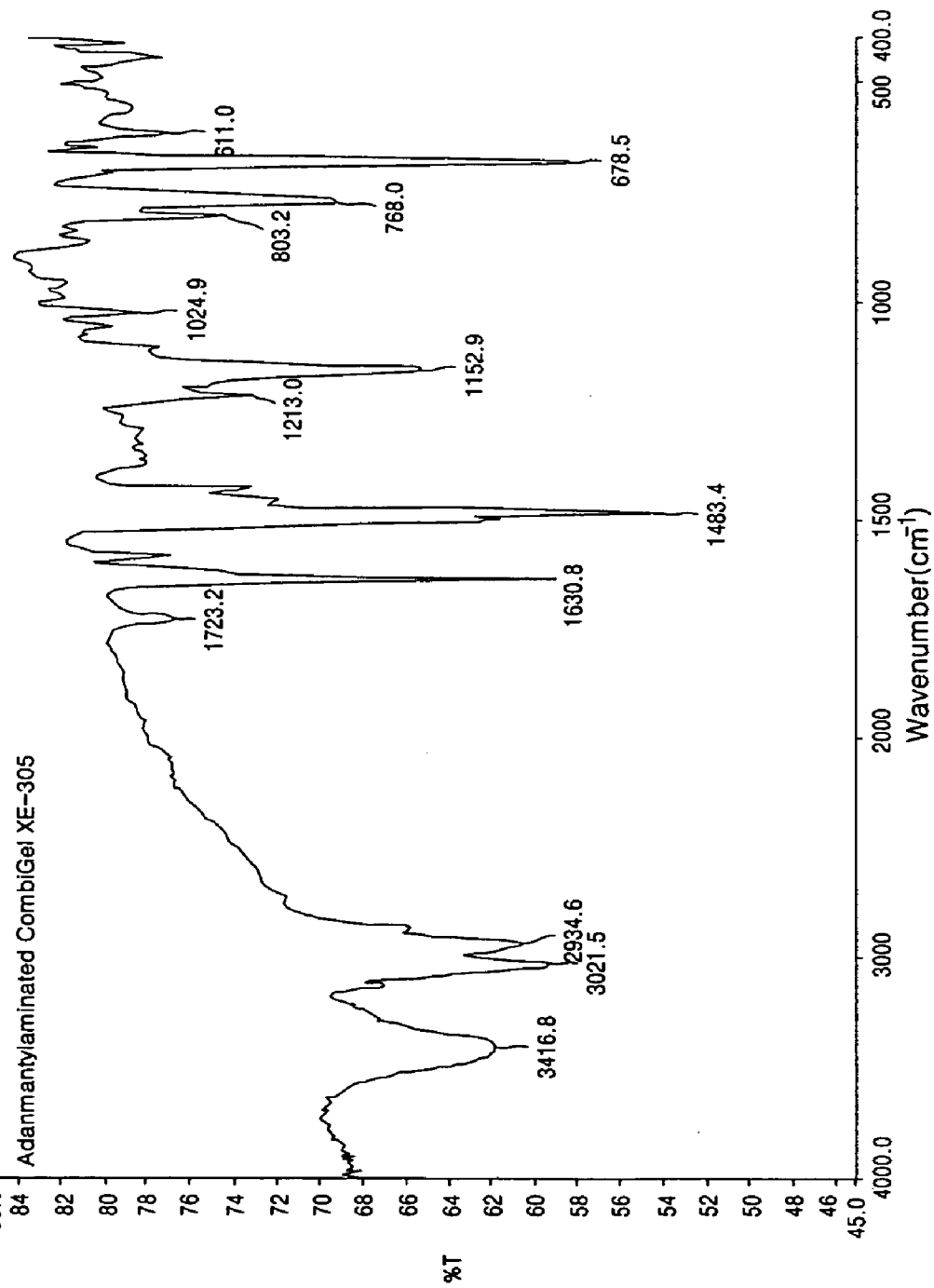
FIG. 21 is the IR spectrum of the adamantylaminated CombiGel XE-305.

IR spectrum (refer to FIG. 21): 3022, 2935, 1630, 1483, 1213, 1153 $cm^{-1}$ (2) Separation of Cucurbit[7]uril Using Affinity Chromatography 1.0 g of the adamantylaminated CombiGel XE-305 (chloromethylated) obtained in (1) above was put into a 10-mL disposable syringe, and about 20 mL of CH2Cl2 was flowed as a solvent. When CH2Cl2/TFA (trifluoroacetic acid) (45 mL/5 mL) was flowed at a rate of 1.3 mL to hydrogenate adamantylamine. Next, 50 mL of CH2Cl2 was flowed at a rate of 2 mL/min to wash the resin, and 50 mL of DMF was flowed at a rate of 0.7 mL/min to swell the resin. 1 g of an unpurified cucurbit[7]uril mixture was dissolved in 30 mL of water and slowly flowed over the resin at a rate of 0.7 mL/min. Next, 50 ml of water was flowed at a rate of 2 mL/min and then 50 mL of methanol was flowed at a rate of 0.7 mL/min to wash the resin. DMF/TEA (triethylamine) (40 mL/20 mL) or an ammonium bicarbonate solution was flowed at a rate of 2 mL/min to separate the cucurbit[7]uril from the resin. Next, 60 mL of water was flowed at a rate of 2 mL/min to separate the cucurbit[7]uril from the resin. The two solutions(DMF/ TEA (triethylamine) (40 mL/20 mL) or an ammonium bicarbonate solution and water solution) were concentrated to obtain a white solid material, and the white solid material was washed with methanol to obtain 240 mg of a final white solid material.

It was confirmed from 1H NMR data that the obtained white solid material was pure cucurbit[7]uril (having formula (2) where each of A1 and A2 is H, X=O, and n=7) not containing any homologues.

Cucurbit[7]uril: $^1$H NMR (300 MHz, $D_2O$): δ=5.79 (d, J=15.4 Hz, 14H), 5.57 (s, 14H), 4.28 (d, J=15.4 Hz, 14H).

In addition, the cucurbit[7]uril mixture was purified in the same manner as above except that the ferrocene-methylaminated Combigel XE-305 obtained in (1) of Example 10, instead of the adamantylaminated CombiGel XE-305, was used. The same results as above are obtained.

(3) Separation of Hydroxycucurbit[7]uril Using Affinity Chromatography

The hydroxycucurbit[7]uril synthesized in Example 2 contained a large amount of potassium salt. To obtain pure hydroxycucurbit[7]uril (having formula (1) where both A1 and A2 are OH, X=O, and n=7), the hydroxycucurbit[7]uril mixture was dissolved in water and passed through the anamantylaminated CombiGel XE-305 resin. Pure hydroxycucurbit[7]uril was separated in the same manner as in (2).

Hydroxycucurbit[7]uril: $^1$H NMR (300 MHz, $D_2O$): δ=7.83 (s, 14H), 5.33 (d, 14H), 4.42 (d, 14H)

In addition, the hydroxycucurbit[7]uril mixture was purified in the same manner as above except that the ferrocene-methylaminated Combigel XE-305 obtained in (1) of Example 10, instead of the adamantylaminated CombiGel XE-305, was used. The same results as above are obtained.

(4) Purification of Cucurbit[N]urils Having Different Substituents Using Affinity Chromatography A perhydroxycucurbit[7]uril mixture, a di-meta-aminophenyl cucurbit[7]uril mixture, a dimethyl cucurbit[7]uril mixture, a cucurbit[8]uril mixture, a hydroxycucurbit[8]uril mixture, a cyclohexanocucurbit[7]uril mixture, a di-p-methoxyphenyl cucurbit[7]uril mixture, and a di-p-hydroxyphenyl cucurbit[7]uril mixture were purified using the affinity chromatography used to purify the cucurbituril[7] in (2) above. As a result, it was confirmed that all the cucurbituriles were purified.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A kit comprising:
   a first component that is a compound of formula (1) below bound to a first material; and
   a second component that is a ligand bound to a second material,
   wherein each of the first and second materials is independently selected from the group consisting of a solid phase, a biomolecule, an antioxidant, a chemical therapeutic agent, an anti-histaminic agent, a cucurbituril dendrimer, a cyclodextrin derivative, a crown ether derivative, a calixarene derivative, a cyclophane derivative, a cyclic peptide derivative, a metallic ion, a chromophore, a fluorescent material, a phosphor, a radioactive material, and a catalyst; and
   the ligand can non-covalently bind to the compound of formula (1) below, has at least one amine group, and is selected from the group consisting of a $C_1$-$C_{20}$ alkyl group; a $C_2$-$C_{20}$ alkenyl group; a $C_2$-$C_{20}$ alkynyl group; a $C_1$-$C_{20}$ alkoxy group; a $C_1$-$C_{20}$ aminoalkyl group; a $C_4$-$C_{20}$ cycloalkyl group; a $C_4$-$C_7$ heteroarylcyclo group; a $C_6$-$C_{20}$ aryl group; a $C_5$-$C_{20}$ heteroaryl group; a $C_1$-$C_{20}$ alkylsilyl group; a $C_6$-$C_{20}$ aryl group; a $C_5$-$C_{20}$ heteroaryl group; adamantane having a substituted or non-substituted $C_1$-$C_{20}$ alkyl group, $C_6$-$C_{20}$ aryl group or $C_5$-$C_{20}$ heteroaryl group; ferrocene or metallocene having a substituted or non-substituted $C_1$-$C_{20}$ alkyl group, $C_6$-$C_{20}$ aryl group or $C_5$-$C_{20}$ heteroaryl group; carborane having a substituted or non-substituted $C_1$-$C_{20}$ alkyl group, $C_6$-$C_{20}$ aryl group or $C_5$-$C_{20}$ heteroaryl group; fullerene having a substituted or non-substituted $C_1$-$C_{20}$ alkyl group, $C_6$-$C_{20}$ aryl group or $C_5$-$C_{20}$ heteroaryl group; cyclam or crown ether having a substituted or non-substituted $C_1$-$C_{20}$ alkyl group, $C_6$-$C_{20}$ aryl group or $C_5$-$C_{20}$ heteroaryl group; an oxygen-protected amino acid having a substituted or non-substituted $C_1$-$C_{20}$ alkyl group, $C_6$-$C_{20}$ aryl group or $C_5$-$C_{20}$ heteroaryl group; peptide having a substituted or non-substituted $C_1$-$C_{20}$ alkyl group, $C_6$-$C_{20}$ aryl group or $C_5$-$C_{20}$ heteroaryl group; alkaloid having a substituted or non-substituted $C_1$-$C_{20}$ alkyl group, $C_6$-$C_{20}$ aryl group or $C_5$-$C_{20}$ heteroaryl group; cisplatin having a substituted or non-substituted $C_1$-$C_{20}$ alkyl group, $C_6$-$C_{20}$ aryl group or $C_5$-$C_{20}$ heteroaryl group; oligonucleotide having a substituted or non-substituted $C_1$-$C_{20}$ alkyl group, $C_6$-$C_{20}$ aryl group or $C_5$-$C_{20}$ heteroaryl group; rhodamine having a substituted or non-substituted $C_1$-$C_{20}$ alkyl group, $C_6$-$C_{20}$ aryl group or $C_5$-$C_{20}$ heteroaryl group; and a nanoparticle having a substituted or non-substituted $C_1$-$C_{20}$ alkyl group, $C_6$-$C_{20}$ aryl group or $C_5$-$C_{20}$ heteroaryl group,

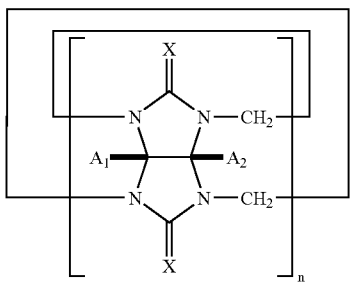

(1)

where n is an integer from 6 to 10;
X is O, S or NH;
each of $A_1$ and $A_2$ is independently H, OR, SR, or NHR, and $A_1$ and $A_2$ are not simultaneously H,
where R is selected from the group consisting of H; a substituted or non-substituted $C_1$-$C_{30}$ alkyl group; a substituted or non-substituted $C_2$-$C_{30}$ alkenyl group; a substituted or non-substituted $C_2$-$C_{30}$ alkynyl group; a substituted or non-substituted $C_2$-$C_{30}$ carbonylalkyl group; a substituted or non-substituted $C_1$-$C_{30}$ thioalkyl group; a substituted or non-substituted $C_1$-$C_{30}$ alkylthiol group; a substituted or non-substituted $C_1$-$C_{30}$ hydroxyalkyl group; a substituted or non-substituted $C_1$-$C_{30}$ alkylsilyl group; a substituted or non-substituted $C_1$-$C_{30}$ aminoalkyl group; a substituted or non-substituted $C_1$-$C_{30}$ aminoalkylthioalkyl group; a substituted or non-substituted $C_5$-$C_{30}$ cycloalkyl group; a substituted or non-substituted $C_2$-$C_{30}$ heterocycloalkyl group; a substituted or non-substituted $C_6$-$C_{30}$ aryl group; a substituted or non-substituted $C_6$-$C_{30}$ arylalkyl group; a substituted or non-substituted $C_4$-$C_{30}$ heteroaryl group; and a substituted or non-substituted $C_4$-$C_{30}$ heteroarylalkyl group.

2. The kit of claim 1, wherein one of the first and second materials is a biomolecule, and the other is a chromophore, a fluorescent material, or a phosphor.

3. The kit of claim 1, wherein the solid phase is a solid support selected from the group consisting of a polymer, a resin, a magnetic material, a silicagel, a polymer- or gold-coated silicagel, a zirconium oxide, a monolithic polymer, a polymer-coated magnetic particle, a gold thin film, a silver thin film, glass, an ITO-coated glass, silicon, a metal electrode, a nanorod, a nanotube, a nanowire, curdlan gum, cellulose, a nylon film, sepharose, and sephadex.

4. The kit of claim 3, wherein the solid phase is polystyrene resin or polymer-coated silicagel.

5. The kit of claim 1, wherein the biomolecule is selected from the group consisting of an enzyme, a nucleic acid, a protein, an amino acid, an antibody, an antigen, an inhibitor, a vitamin, a cofactor, a fatty acid, a cell, a cell membrane, a substrate, a substrate analogue, a suppressor, a coenzyme, a virus, lectin, a polysaccharide, a glucoprotein, a receptor, histone, ATP, ADP, a hormone, a receptor, and glutathione.

6. The kit of claim 5, wherein the enzyme is selected from the group consisting of cellulase, hemicellulase, peroxidase, protease, amylase, xylanase, lipase, esterase, cutinase, pectinase, keratinase, reductase, oxidase, phenoloxidase, lipoxigenase, ligninase, pullulanase, arabinosidase, hyaluronidase, and a combination thereof.

7. The kit of claim 1, wherein the catalyst is a Grobbs catalyst, a radical initiator, or a combination thereof.

8. The kit of claim 1, wherein, in said formula (1), each of $A_1$ and $A_2$ is independently H, OR, SR, or NHR where R is a substituted or non-substituted $C_2$-$C_{30}$ alkenyl group.

9. The kit of claim 1, wherein, in said formula (1), n is 7, and X is O.

10. The kit of claim 1, wherein the ligand is adamantane, ferrocene, or metallocene that have at least one amine group and a substituted or non-substituted $C_1$-$C_{20}$ alkyl group, $C_6$-$C_{20}$ aryl group or $C_5$-$C_{20}$ heteroaryl group.

11. The kit of claim 10, wherein the amine group is a primary amine, a secondary amine, or a hydrogenated amine.

12. The kit of claim 10, wherein the ligand is adamantanamine or ferrocene methylamine.

* * * * *